United States Patent
Elkins et al.

(10) Patent No.: US 7,713,266 B2
(45) Date of Patent: *May 11, 2010

(54) SUBDERMAL CRYOGENIC REMODELING OF MUSCLES, NERVES, CONNECTIVE TISSUE, AND/OR ADIPOSE TISSUE (FAT)

(75) Inventors: Lisa Elkins, Woodside, CA (US); Ronald Williams, Menlo Park, CA (US)

(73) Assignee: Myoscience, Inc., Redwood City, CA (US)

( * ) Notice: Subject to any disclaimer, the term of this patent is extended or adjusted under 35 U.S.C. 154(b) by 1022 days.

This patent is subject to a terminal disclaimer.

(21) Appl. No.: 11/295,204

(22) Filed: Dec. 5, 2005

(65) Prior Publication Data
US 2007/0129714 A1    Jun. 7, 2007

Related U.S. Application Data

(60) Provisional application No. 60/683,393, filed on May 20, 2005.

(51) Int. Cl.
*A61B 18/02* (2006.01)
(52) U.S. Cl. .............................. 606/21; 606/20; 606/22; 606/23; 606/24; 607/105; 607/113
(58) Field of Classification Search ............. 600/20–26; 606/20–26; 607/105, 107, 113
See application file for complete search history.

(56) References Cited

U.S. PATENT DOCUMENTS 2,319,542 A    5/1943    Hall
2,672,032 A    3/1954    Towse (Continued)

FOREIGN PATENT DOCUMENTS

CA    2 643 474    9/2007

(Continued)

OTHER PUBLICATIONS

Yange, Weng-Lang Yang, et al. Apoptosis induced by cryo-injury in human colorectal cancer cells is associated with mitochondrial dysfunction. International Journal of Cancer,2002, vol. 103, No. 3, pp. 360-369. MEDLINE [online]. [retrieved on Apr. 2, 2009]. Retrieved from: MEDLINE.*

(Continued)

*Primary Examiner*—Lee S Cohen
*Assistant Examiner*—Jaymi Della
(74) *Attorney, Agent, or Firm*—Townsend and Townsend and Crew LLP

(57) ABSTRACT

Devices, systems, and methods treat cosmetic defects, and often apply cooling with at least one tissue-penetrating probe inserted through of the skin of a patient. The cooling may remodel one or more target tissue so as to effect a desired change in a composition of the target tissue and/or a change in its behavior. Exemplary embodiments of the cooling treatments will interfere with the nerve/muscle contractile function chain so as to mitigate wrinkles of the skin. Related treatments may be used therapeutically for treatment of back and other muscle spasms, chronic pain, and the like. Some embodiments may remodel subcutaneous adipose tissue so as to alter a shape or appearance of the skin surface.

27 Claims, 12 Drawing Sheets

U.S. PATENT DOCUMENTS

| | | | |
|---|---|---|---|
| 3,226,492 A | 12/1965 | Steinberg | |
| 3,507,283 A | 4/1970 | Thomas, Jr. | |
| 3,664,344 A | 5/1972 | Bryne | |
| 3,886,945 A | 6/1975 | Stumpf et al. | |
| 3,889,681 A | 6/1975 | Waller et al. | |
| 3,951,152 A | 4/1976 | Crandell et al. | |
| 3,993,075 A | 11/1976 | Lisenbee et al. | |
| 4,140,109 A | 2/1979 | Savic et al. | |
| 4,207,897 A * | 6/1980 | Lloyd et al. | 606/23 |
| 4,306,568 A | 12/1981 | Torre | |
| 4,376,376 A | 3/1983 | Gregory | |
| 4,524,771 A | 6/1985 | McGregor et al. | |
| 4,758,217 A | 7/1988 | Gueret | |
| 4,802,475 A | 2/1989 | Weshahy | |
| 4,946,460 A | 8/1990 | Merry et al. | |
| 5,200,170 A | 4/1993 | McDow | |
| 5,334,181 A | 8/1994 | Rubinsky et al. | |
| 5,571,147 A | 11/1996 | Sluijter et al. | |
| 5,647,868 A | 7/1997 | Chinn | |
| 5,755,753 A | 5/1998 | Knowlton | |
| 5,814,040 A | 9/1998 | Nelson et al. | |
| 5,899,897 A | 5/1999 | Rabin et al. | |
| 5,916,212 A | 6/1999 | Baust et al. | |
| 5,976,505 A | 11/1999 | Henderson | |
| 6,003,539 A | 12/1999 | Yoshihara | |
| 6,032,675 A * | 3/2000 | Rubinsky | 128/898 |
| 6,039,730 A | 3/2000 | Rabin et al. | |
| 6,041,787 A | 3/2000 | Rubinsky | |
| 6,139,545 A | 10/2000 | Utley et al. | |
| 6,141,985 A | 11/2000 | Cluzeau et al. | |
| 6,196,839 B1 | 3/2001 | Ross | |
| 6,277,116 B1 | 8/2001 | Utely et al. | |
| 6,432,102 B2 * | 8/2002 | Joye et al. | 606/21 |
| 6,494,844 B1 | 12/2002 | Van Bladel et al. | |
| 6,503,246 B1 | 1/2003 | Har-Shai et al. | |
| 6,506,796 B1 | 1/2003 | Fesus et al. | |
| 6,546,935 B2 | 4/2003 | Hooven | |
| 6,551,309 B1 | 4/2003 | LePivert | |
| 6,562,030 B1 | 5/2003 | Abboud et al. | |
| 6,669,688 B2 | 12/2003 | Svaasand et al. | |
| 6,672,095 B1 | 1/2004 | Luo | |
| 6,706,037 B2 * | 3/2004 | Zvuloni et al. | 606/21 |
| 6,749,624 B2 | 6/2004 | Knowlton | |
| 6,761,715 B2 | 7/2004 | Carroll | |
| 6,764,493 B1 | 7/2004 | Weber et al. | |
| 6,786,902 B1 | 9/2004 | Rabin et al. | |
| 6,789,545 B2 | 9/2004 | Littrup et al. | |
| 6,858,025 B2 | 2/2005 | Maurice | |
| 6,905,492 B2 | 6/2005 | Zvuloni et al. | |
| 7,001,400 B1 | 2/2006 | Modesitt et al. | |
| 7,081,111 B2 | 7/2006 | Svaasand et al. | |
| 7,083,612 B2 | 8/2006 | Littrup et al. | |
| 7,367,341 B2 | 5/2008 | Anderson et al. | |
| 2002/0013602 A1 | 1/2002 | Huttner | |
| 2002/0128638 A1 * | 9/2002 | Chauvet et al. | 606/21 |
| 2002/0183731 A1 | 12/2002 | Holland et al. | |
| 2002/0193778 A1 | 12/2002 | Alchas et al. | |
| 2003/0036752 A1 | 2/2003 | Joye et al. | |
| 2003/0109912 A1 | 6/2003 | Joye et al. | |
| 2003/0181896 A1 | 9/2003 | Zvuloni et al. | |
| 2004/0122482 A1 | 6/2004 | Tung et al. | |
| 2004/0162551 A1 | 8/2004 | Brown et al. | |
| 2004/0167505 A1 | 8/2004 | Joye et al. | |
| 2004/0191229 A1 | 9/2004 | Link et al. | |
| 2004/0204705 A1 | 10/2004 | Lafontaine | |
| 2004/0210212 A1 | 10/2004 | Maurice | |
| 2004/0215178 A1 | 10/2004 | Maurice | |
| 2004/0215294 A1 | 10/2004 | Littrup et al. | |
| 2004/0225276 A1 | 11/2004 | Burgess | |
| 2004/0243116 A1 | 12/2004 | Joye et al. | |
| 2005/0177147 A1 | 8/2005 | Vancelette et al. | |
| 2005/0177148 A1 | 8/2005 | van der Walt et al. | |
| 2005/0203505 A1 | 9/2005 | Megerman et al. | |
| 2005/0203593 A1 | 9/2005 | Shanks | |
| 2005/0209565 A1 | 9/2005 | Yuzhakov et al. | |
| 2005/0209587 A1 | 9/2005 | Joye et al. | |
| 2005/0228288 A1 | 10/2005 | Hurst | |
| 2005/0261753 A1 | 11/2005 | Littrup et al. | |
| 2005/0276759 A1 | 12/2005 | Roser et al. | |
| 2005/0283148 A1 | 12/2005 | Janssen et al. | |
| 2006/0009712 A1 | 1/2006 | Van Bladel et al. | |
| 2006/0015092 A1 | 1/2006 | Joye et al. | |
| 2006/0069385 A1 | 3/2006 | Lafontaine et al. | |
| 2006/0079914 A1 | 4/2006 | Modesitt et al. | |
| 2006/0084962 A1 | 4/2006 | Joye et al. | |
| 2006/0111732 A1 | 5/2006 | Gibbens et al. | |
| 2006/0129142 A1 | 6/2006 | Reynolds | |
| 2006/0142785 A1 | 6/2006 | Modesitt et al. | |
| 2006/0173469 A1 | 8/2006 | Klein et al. | |
| 2006/0189968 A1 | 8/2006 | Howlett et al. | |
| 2006/0190035 A1 | 8/2006 | Hushka et al. | |
| 2006/0200117 A1 | 9/2006 | Hermans | |
| 2006/0212028 A1 | 9/2006 | Joye et al. | |
| 2006/0212048 A1 | 9/2006 | Crainich | |
| 2006/0223052 A1 | 10/2006 | MacDonald et al. | |
| 2007/0060921 A1 | 3/2007 | Janssen et al. | |
| 2007/0088217 A1 | 4/2007 | Babaev | |
| 2007/0156125 A1 | 7/2007 | DeLonzor | |
| 2007/0161975 A1 | 7/2007 | Goulko | |
| 2007/0167943 A1 | 7/2007 | Janssen et al. | |
| 2007/0167959 A1 | 7/2007 | Modesitt et al. | |
| 2007/0179509 A1 | 8/2007 | Nagata et al. | |
| 2007/0198071 A1 | 8/2007 | Ting et al. | |
| 2007/0255362 A1 | 11/2007 | Levinson et al. | |
| 2007/0270925 A1 | 11/2007 | Levinson | |
| 2008/0077201 A1 | 3/2008 | Levinson et al. | |
| 2008/0077202 A1 | 3/2008 | Levinson | |
| 2008/0077211 A1 | 3/2008 | Levinson et al. | |
| 2008/0154254 A1 | 6/2008 | Burger et al. | |
| 2008/0183164 A1 | 7/2008 | Elkins et al. | |
| 2008/0200910 A1 | 8/2008 | Burger et al. | |
| 2008/0287839 A1 | 11/2008 | Rosen et al. | |
| 2009/0018623 A1 | 1/2009 | Levinson et al. | |
| 2009/0018624 A1 | 1/2009 | Levinson et al. | |
| 2009/0018625 A1 | 1/2009 | Levinson et al. | |
| 2009/0018626 A1 | 1/2009 | Levinson et al. | |
| 2009/0018627 A1 | 1/2009 | Levinson et al. | |

FOREIGN PATENT DOCUMENTS

| | | |
|---|---|---|
| EP | 0043447 A2 | 6/1981 |
| EP | 1377327 B1 | 9/2007 |
| EP | 1 862 125 | 12/2007 |
| GB | 1402632 | 8/1975 |
| JP | 10-014656 | 1/1998 |
| JP | 2006-130055 | 5/2006 |
| RU | 2254060 | 6/2005 |
| WO | WO 97/49344 | 12/1997 |
| WO | WO 01/97702 | 12/2001 |
| WO | WO 2004/089460 | 10/2004 |
| WO | WO 2005/000106 | 1/2005 |
| WO | WO 2006/012128 | 2/2006 |
| WO | WO 2006/023348 | 3/2006 |
| WO | WO 2006/125835 | 11/2006 |
| WO | WO 2007/037326 | 4/2007 |
| WO | WO 2007/089603 | 8/2007 |
| WO | WO 2007/129121 | 11/2007 |
| WO | WO 2007/135629 | 11/2007 |
| WO | WO 2009/026471 | 2/2009 |

OTHER PUBLICATIONS

Dasiou-Plakida, D. "Fat injections for facial rejuvenation: 17 years experience in 1720." Journal of Cosmetic Dermatology 2.3-4 (2004):

119-125. Web. Sep 28, 2009. <http://www3.interscience.wiley.com/cgi-bin/fulltext/118899715/PDFSTART>.*

Rutkove, Seward B. (2001). Effects of temperature on neuromuscular electrophysiology. Muscle & Nerve, 24; p. 867-882. Retrieved from http://www3.interscience.wiley.com/cgi-bin/fulltext/83502418/PDFSTART.*

International Search Report of PCT Application PCT/US07/87893, issued Jun. 18, 2008, 14 pages total.

International Search Report and Written Opinion of PCT Application No. PCT/US08/53876, dated Aug. 15, 2008, 16 pages total.

Extended European Search Report and Search Opinion of EP Application No. 06770671.3, mailed Sep. 22, 2009, 14 pages total.

Har-Shai et al., "Effect of skin surface temperature on skin pigmentation during contact and intralesional cryosurgery of hypertrophic scars and Kleoids," Journal of the European Academy of Dermatology and Venereology 21 (2):191-198. Feb. 2007.

International Preliminary Report on Patentability of PCT Application, issued Nov. 23, 2007, 4 pages total.

Cryopen, LLC [Press Release], "CryoPen, LLC Launches Revolutionary, State-of-the-Art Medical Device—The Dure of Cryosurgery in a Pend," dated Apr. 27, 2007, retrieved from the Internet: <<http://cryopen.com/press. htm>>, 3 pages total.

Cryopen, LLC., [webpage], retrieved from the Interent: <<http://cryopen.com/>>, copyright 2006-2008, 2 pages total.

One Med Group, LLC., [webpage] "CryoProbe™", retrieved from the Internet: <<http://www.onemedgroup.com/>> on Feb. 8, 2008, 2 pages total.

Cryosurgical Concepts, Inc., [webpage] "CryoProbe™", retrieved from the Internet: <<http://www.cryo-surgical.com//>> on Feb. 8, 2008, 2 pages total.

Advanced Cosmetic Intervention, Inc. [webpage], retrieved from the Internet: <<http://www.acisurgery.com>>, copyright 2007, 1 page.

U.S. Appl. No. 11/614,887, filed Dec. 21, 2006; first named inventor: Keith Burger.

U.S. Appl. No. 11/675,886, filed Feb. 16, 2007; first named inventor: Keith Burger.

U.S. Appl. No. 11/770,185, filed Jun. 28, 2007; first named inventor: Lisa Elkins.

Utley et al., "Radiofrequency Ablation of the Nerve to the Corrugator Muscle for the Elimination of Glabellar Furrowing," Arch. Facial Plastic Surgery 1: 46-48, 1999.

* cited by examiner

FIG. 2C M (Oticularis)

FIG. 2D N (Frontalis)

FIG. 2E O (Orbicularis)

FIG. 2F P (Mentalis)

FIG. 2G Q (Platysma)

SUBDERMAL CRYOGENIC REMODELING OF MUSCLES, NERVES, CONNECTIVE TISSUE, AND/OR ADIPOSE TISSUE (FAT)

CROSS-REFERENCES TO RELATED APPLICATIONS

This present application is a regular utility application which claims the benefit of priority from U.S. Provisional Patent Application No. 60/683,393 filed on May 20, 2005.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

The present invention is generally directed to medical devices, systems, and methods, particularly for improving the appearance of a patient and other applications. Embodiments of the invention include devices, systems, and methods for applying cryogenic energy to subcutaneous tissues so as to selectively remodel one or more target tissues below an exposed surface of the skin, often by inhibiting undesirable and/or unsightly effects on the skin (such as lines, wrinkles, or cellulite dimples) or on other surrounding tissue. The remodeling of the target tissue may achieve a desired change in its behavior or composition, and will often help alleviate cosmetically undesirable characteristics.

The desire to reshape various features of the human body to either correct a deformity or merely to enhance one's appearance is common. This is evidenced by the growing volume of cosmetic surgery procedures that are performed annually.

Many procedures are intended to change the surface appearance of the skin by reducing lines and wrinkles. Some of these procedures involve injecting fillers or stimulating collagen production. More recently, pharmacologically based therapies for wrinkle alleviation and other cosmetic applications have gained in popularity.

Botulinum toxin type A (BOTOX®) is an example of a pharmacologically based therapy used for cosmetic applications. It is typically injected into the facial muscles to block muscle contraction, resulting in temporary innervation or paralysis of the muscle. Once the muscle is disabled, the movement contributing to the formation of the undesirable wrinkle is temporarily eliminated. Another example of pharmaceutical cosmetic treatment is mesotherapy, where a cocktail of homeopathic medication, vitamins, and/or drugs approved for other indications is injected into the skin to deliver healing or corrective treatment to a specific area of the body. Various cocktails are intended to effect body sculpting and cellulite reduction by dissolving adipose tissue, or skin resurfacing via collagen enhancement. Development of non-pharmacologically based cosmetic treatments also continues. For example, endermology is a mechanical based therapy that utilizes vacuum suction to stretch or loosen fibrous connective tissues which are implicated in the dimpled appearance of cellulite.

While BOTOX® and/or mesotherapies may temporarily reduce lines and wrinkles, reduce fat, or provide other cosmetic benefits they are not without their drawbacks, particularly the dangers associated with injection of a known toxic substance into a patient, the potential dangers of injecting unknown and/or untested cocktails, and the like. Additionally, while the effects of endermology are not known to be potentially dangerous, they are brief and only mildly effective.

In light of the above, it would be desirable to provide improved medical devices, systems, and methods, particularly for treatment of wrinkles, fat, cellulite, and other cosmetic defects. It would be particularly desirable if these new techniques provided an alternative visual appearance improvement mechanism which could replace and/or compliment known bioactive and other cosmetic therapies, ideally allowing patients to decrease or eliminate the injection of toxins and harmful cocktails while providing similar or improved cosmetic results. It would also be desirable if such techniques were performed percutaneously using only local or no anesthetic with minimal or no cutting of the skin, no need for suturing or other closure methods, no extensive bandaging, and limited or no bruising or other factors contributing to extended recovery or patient "down time".

BRIEF SUMMARY OF THE INVENTION

The present invention generally provides improved medical devices, systems, and methods for the treatment of cosmetic defects and other applications. Embodiments of the present invention apply cooling with at least one probe inserted through an exposed surface of the skin of a patient. The cooling may remodel one or more target tissue so as to effect a desired change in a composition of the target tissue and/or a change in its behavior. Exemplary embodiments of the cooling treatments will interfere with the nerve/muscle contractile function chain so as to mitigate wrinkles of the skin, and related treatments may be used therapeutically for treatment of back and other muscle spasms, chronic pain, and the like. Some embodiments may remodel subcutaneous adipose tissue or fibrous connective tissue so as to alter a shape or appearance of the skin surface.

Optionally, cooling times, temperatures, pressures, cooling fluid vaporization or the like may be configured to provide a desired or variably selectable efficacy time. Treatments at moderate temperatures (for example at temperatures which only temporarily stun tissues but do not induce significant apoptosis or necrosis) may have only short term muscle contraction inhibiting effects. Other treatments may be longer lasting, optionally being permanent. Fibroblastic response-based efficacy may, in some embodiments, be self-limiting. Probe, applicator, and/or controller designs may allow treatments by persons with limited skill and training, so that efficacy is not operator dependent. In some embodiments, no foreign bodies and/or materials will be left behind. Other embodiments may employ materials such as bioactive agents, warmed saline, or the like to limit injury and/or enhance remodeling efficacy, with some treatments being combined with pharmaceuticals such as BOTOX® compounds or the like. Similarly, no tissue will be required to be removed to achieve the desired affect in many embodiments. Advantageously, the cooling probe, a single-use cooling fluid cartridge, and controller may be included in a disposable (often non-sterilizable) self-contained treatment system that may limit capital investment and facilitate treatments in third-world environments.

In a first aspect, the invention provides a method for improving a cosmetic appearance of a patient. The patient has a skin surface, and the method comprises inserting a probe through the skin surface and cooling a target tissue below the skin surface such that the target tissue is remodeled. The remodeling of the target tissue alters a shape of the skin surface.

In many cases, prior to remodeling the skin surface will exhibit lines or wrinkles. Contraction of sub-dermal muscles and the associated movement of the skin may contribute to the development and appearance of these lines or wrinkles, and the remodeling can be performed so as to reduce or eliminate this contraction and/or movement, effectively smoothing the lines or wrinkles. The skin surface will often include a region of the face, with the target tissues optionally comprising a muscle, a nerve, connective tissue, nerve/muscle junction, and/or the like associated with that muscle. The cooling may inhibit contraction of the muscle so as to improve an appearance of the patient.

In many embodiments, a cooling-induced injury of the skin surface may be inhibited such that the target tissue is selectively cooled. For example, warming energy may be applied along the skin surface, optionally by heating the skin surface with an applicator of the probe before, during, and/or after cooling of the target tissue. A material which inhibits cooling injury may also be disposed along the skin surface during cooling, such as a heated biocompatible fluid, a biocompatible cryoprotectant (optionally comprising dimethylsulfoxide ("DMSO"), propylene glycol, and/or glycerol). In some embodiments, injury to the skin surface may be inhibited by applying a cooling injury enhancing material to the target tissue so that overall cooling and damage to the skin may be limited. It will often be desirable to limit injury to the skin surface sufficiently to avoid permanently altering a color of the skin surface, and/or to limit or avoid visible necrosis of the dermal tissues along the skin surface.

In some embodiments, the skin surface may have an uneven cellulite or other adipose tissue-induced texture and/or shape. The remodeling may be performed so as to smooth such a texture so as to improve the appearance of the patient. Optionally, the cooling may be performed so as to induce a reduction in tissue mass after removal of the probe from the patient. The reduction in tissue mass may occur as part of a tissue response to the cooling, optionally as part of the healing process, and the reduction in tissue mass may at least help provide a desired change in the shape of the skin surface. For example, where the tissue comprises an adipose tissue, a healing response to the cooling may decrease a mass of the adipose tissue by inducing adipose tissue restoration. In other embodiments, the cooling may reduce muscle mass, particularly of muscles of the face which are associated with lines and wrinkles.

In general, the target tissue may be cooled to a temperature from about 10° C. to about −40° C., with the target tissue optionally being cooled to a temperature in a range from about 0° C. to about −15° C. More moderate treatment temperatures (for example, warmer than about −5° C.) and briefer treatment times may provide temporary efficacy, while colder treatment temperatures (for example, at about −5° C. or cooler) and longer treatment times may result in permanent changes to the target tissue and/or skin surface shape. Surprisingly, within some treatment temperature ranges, warmer treatments may provide more long-term or even permanent efficacy, while colder treatment temperatures may result in temporary changes to the target tissue and skin surface shape. For example, in some embodiments long-term or permanent efficacy of the treatment may be provided through apoptosis (sometimes referred to as programmed cell death). In contrast, necrosis-based effects may be reduced or eliminated with healing. Apoptosis can reduce muscle mass or disrupt the chain of contractility without inducing inflammation and triggering of the satellite cells that may be involved in the skeletal muscle repair process. Alternative mechanisms may also be involved, including a temporary and/or permanent loss of elasticity in muscle tissues through changes in morphology of collagen and/or elastin with ice formation, necrosis, a loss of elasticity in the fibrous connective tissue, impairment of signal transmission along the neural pathways, blocking production of acetylcholine (or other chemicals pertinent to contractility) or disrupting conductivity, hypoxia (optionally by cutting-off of the blood supply to a muscle or other tissue in the contractile chain through apoptosis or some other mechanism), or the like.

Advantageously, a permanent or temporary effect may be selected, with even the duration of the effect optionally being selected by the patient and/or system user, allowing (for example) an initially temporary treatment to be performed so as to verify the desirability of the results prior to implementing a long lasting or permanent treatment. In some embodiments, smaller doses or regions of a more permanent effect may be delivered sequentially over time in order to achieve a permanent, full effect desired while avoiding drastic, over dosed, or undesirable outcomes.

In many embodiments, a plurality of tissue-penetrating probes may be inserted through the skin surface. Optionally, a separation between adjacent probes may be established so that a cooling effect remodels a desired portion, the majority of, substantially all of, and/or all of the tissues disposed between the probes. Varied amounts of tissue and/or patterns of targeted tissues can provide different desired effects, with the targeted tissues optionally being treated sequentially using a single tissue penetrating probe or the like.

In another aspect, the invention provides a method for improving a cosmetic appearance of a patient. The patient has a skin surface with a muscle therebelow. The muscle has an associated nerve/muscle contractile chain. The chain typically includes, for example, the muscle, a nerve, a connective tissue (such as a ligament, tendon, cartilage, or the like), and/or a nerve/muscle junction, and can also encompass related tissues such as the blood vessels which supply blood to the muscles or the like. The method comprises directing energy or cooling from a probe to a component of the nerve/muscle contractile chain such that the component is remodeled and the remodeling inhibits contraction of the muscle so as to improve the cosmetic appearance of the skin surface.

In another method aspect, the invention provides a method for improving a cosmetic appearance of the patient. The patient has a skin surface with a tissue therebelow. The tissue has a mass, and the method comprises directing sufficient tissue-remodeling energy or cooling from a probe through the skin surface to induce a reduction in the mass of the tissue such that the cosmetic appearance of the skin surface is improved.

In yet another method aspect, the invention provides a method for treating a patient. The patient has a skin surface and a muscle therebelow. The method comprises directing sufficient tissue remodeling energy or cooling below the skin surface so that contraction of the muscle is inhibited or a loss of elasticity is induced. Related methods may comprise applying chemicals, and/or a means of cutting-off the tissue's blood supply.

Along with directing of cooling to (for example) a component of the contractile chain of a muscle, embodiments of the invention may rely at least in part on any of a variety of forms of energy transmissions to these or other tissues so as to inhibit muscle contraction, decrease muscle (or other tissue) mass, and the like. Suitable energy forms that may be used in place of or in conjunction with cooling may include ultrasound energy, radio frequency electrosurgical energy, microwave energy, laser energy, electromagnetic or particle radiation, and the like. Optionally, any of these treatment modalities may be combined with the use of bioactive agents, chemicals, or varied method of cutting off the tissue's blood supply.

In another aspect, the invention provides a system for cosmetically reshaping an exposed skin surface of a patient. The system comprises a probe body having at least one cooling fluid supply path. At least one tissue-penetrating probe extends distally from the body. The at least one probe has a distal tissue-piercing end and is in thermal communication with the at least one cooling fluid supply path. A cooling fluid source is coupled to the at least one cooling fluid supply path so as to cool the at least one probe distally of the body. The cooling may remodel adjacent tissue when the at least one probe is inserted through the skin surface, and the remodeling may reshape the skin surface.

In many embodiments, a controller will be coupled to the cooling fluid path so as to control a treatment time and/or treatment temperature. The controller may have an input for identifying a desired duration of the remodeling, and the controller may determine a characteristic of the cooling in response to the desired duration.

In some embodiments, a cooling region of the probe or probes inserted through the skin surface may have a cooling region for selectively cooling the target tissue, with the cooling region optionally being separated from the proximal end of the insertable probe. For example, an insulated region may extend between the cooling region and a skin engaging surface of the probe body so as to inhibit injury along the skin surface. Materials and/or energy may be directed to tissues along the skin surface or any of a variety of other collateral tissues may be protected.

In another aspect, the invention provides a system for improving a cosmetic appearance of a patient. The patient has skin surface with a tissue therebelow. The tissue has a mass, and the system comprises a probe having a tissue engaging surface directing sufficient tissue-remodeling energy or cooling from the probe through the skin surface to induce a reduction in the mass of the tissue such that the cosmetic appearance of the skin surface is improved.

In yet another system aspect, the invention provides a system for treating a patient. The patient has a skin surface, and a muscle therebelow. The system comprises a transmission surface directing sufficient tissue remodeling energy or cooling below the skin surface so that contraction of the muscle is inhibited.

BRIEF DESCRIPTION OF THE DRAWINGS

FIGS. 2 and 2A-2L illustrates target tissues for treatment in some embodiments of the present invention, along with associated lines or wrinkles and treatment patterns.

DETAILED DESCRIPTION OF THE INVENTION

The present invention provides improved medical devices, system, and methods. Embodiments of the invention will facilitate remodeling of tissues disposed below the skin, often so as to alter a shape of the overlying skin surface, in many cases while inhibiting or avoiding collateral injury to the skin and associated skin scarring, discoloration, and the like.

Among the most immediate applications of the present invention may be the amelioration of lines and wrinkles, particularly by inhibiting muscular contractions which are associated with these cosmetic defects so as so improve an appearance of the patient. Rather than relying entirely on a pharmacological toxin or the like to disable muscles so as to induce temporary paralysis, many embodiments of the invention will at least in part employ cold to immobilize muscles. Advantageously, nerves, muscles, and associated tissues may be temporarily immobilized using moderately cold temperatures of 10° C. to −5° C. without permanently disabling the tissue structures. Using an approach similar to that employed for identifying structures associated with atrial fibrillation, a needle probe or other treatment device can be used to identify a target tissue structure in a diagnostic mode with these moderate temperatures, and the same probe (or a different probe) can also be used to provide a longer term or permanent treatment, optionally by ablating the target tissue zone and/or inducing apoptosis at temperatures from about −5° C. to about −50° C. In some embodiments, apoptosis may be induced using treatment temperatures from about −1° C. to about −15° C., optionally so as to provide a permanent treatment that limits or avoids inflammation and mobilization of skeletal muscle satellite repair cells. Hence, the duration of the treatment efficacy of such subdermal cryogenic treatments may be selected and controlled, with colder temperatures, longer treatment times, and/or larger volumes or selected patterns of target tissue determining the longevity of the treatment.

In addition to cosmetic treatments of lines, wrinkles, and the like, embodiments of the invention may also find applications for treatments of subdermal adipose tissues. Embodiments of the invention may also find applications for alleviation of pain, including those associated with muscle spasms. Still further embodiments may rely on application of energy (with or without cooling) for remodeling of target tissues and producing a desired cosmetic effect, with the energy optionally comprising focused or unfocused ultrasound energy, radio frequency energy, laser energy microwave energy, other electromagnetic or particle radiation, alternative methods of applying heat, chemicals, vascular embolization, and the like. Hence, a variety of embodiments may be provided.

Figure 1A:
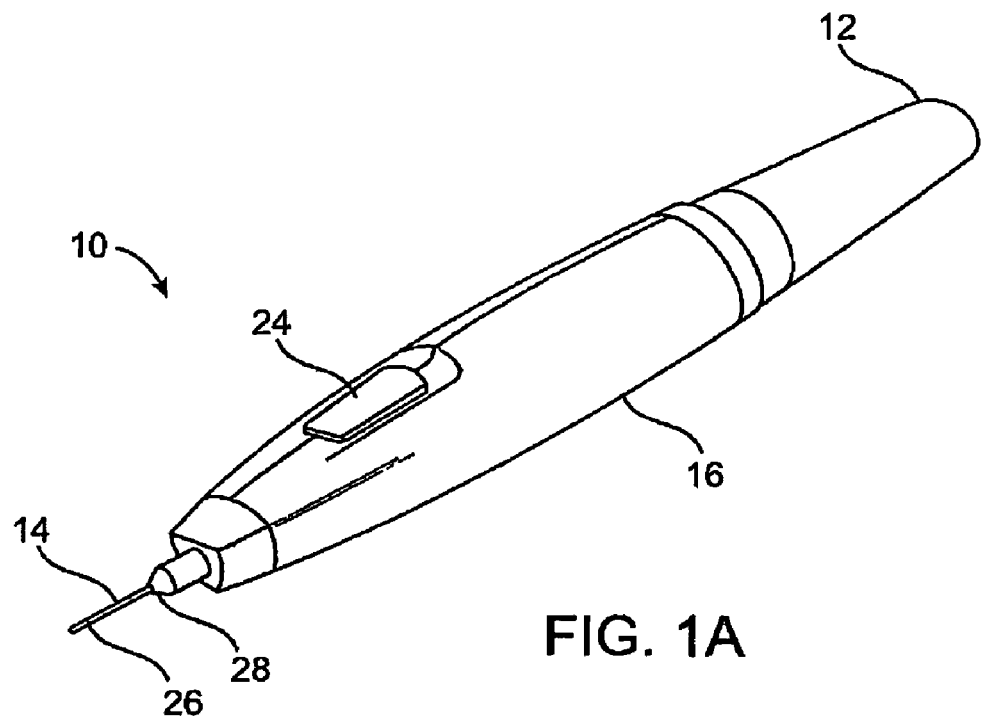
FIG. 1A is a perspective view of a self-contained subdermal cryogenic remodeling probe and system, according to an embodiment of the invention.
Figure 1B:
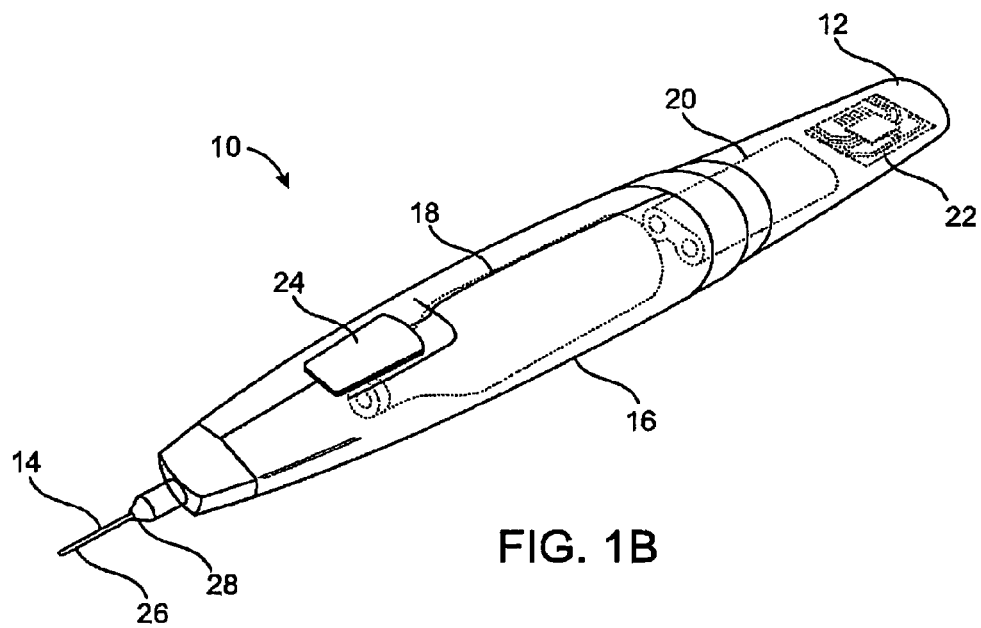
FIG. 1B is a partially transparent perspective view of the self-contained probe of FIG. 1A, showing internal components of the cryogenic remodeling system.

Referring now to FIGS. 1A and 1B, a system for subdermal cryogenic remodeling here comprises a self-contained probe handpiece generally having a proximal end 12 and a distal end 14. A handpiece housing 16 has a size and shape suitable for supporting in a hand of a surgeon or other system operator. As can be seen most clearly in FIG. 1B, a cryogenic cooling fluid supply 18 and electrical power source 20 are found within housing 16, along with a circuit 22 having a processor for controlling cooling applied by self-contained system 10 in response to actuation of an input 24.

Extending distally from distal end 14 of housing 16 is a tissue-penetrating cryogenic cooling probe 26. Probe 26 is thermally coupled to a cooling fluid path extending from cooling fluid source 18, with the exemplary probe comprising a tubular body receiving at least a portion of the cooling fluid from the cooling fluid source therein. The exemplary probe 26 comprises a 30 g needle having a sharpened distal end that is axially sealed. Probe 26 may have an axial length between distal end 14 of housing 16 and the distal end of the needle of between about ½ mm and 5 cm, preferably having a length from about 1 mm to about 3 mm. Such a needles may comprise a stainless steel tube with an inner diameter of about 0.006 inches and an outer diameter of about 0.012 inches, while alternative probes may comprise structures having outer diameters (or other lateral cross-sectional dimensions) from about 0.006 inches to about 0.100 inches.

Addressing some of the components within housing 16, the exemplary cooling fluid supply 18 comprises a cartridge containing a liquid under pressure, with the liquid preferably having a boiling temperature of less than 37° C. When the fluid is thermally coupled to the tissue-penetrating probe 26, and the probe is positioned within the patient so that an outer surface of the probe is adjacent to a target tissue, the heat from the target tissue evaporates at least a portion of the liquid and the enthalpy of vaporization cools the target tissue. A valve (not shown) may be disposed along the cooling fluid flow path between cartridge 18 and probe 26, or along the cooling fluid path after the probe so as to limit the temperature, time, rate of temperature change, or other cooling characteristics. The valve will often be powered electrically via power source 20, per the direction of processor 22. The exemplary power source 20 comprises a rechargeable or single-use battery.

The exemplary cooling fluid supply 18 comprises a single-use cartridge. Advantageously, the cartridge and cooling fluid therein may be stored and/or used at (or even above) room temperature. The cartridges may have a frangible seal or may be refillable, with the exemplary cartridge containing liquid $N_2O$. A variety of alternative cooling fluids might also be used, with exemplary cooling fluids including fluorocarbon refrigerants and/or carbon dioxide. The quantity of cooling fluid contained by cartridge 18 will typically be sufficient to treat at least a significant region of a patient, but will often be less than sufficient to treat two or more patients. An exemplary liquid $N_2O$ cartridge might contain, for example, a quantity in a range from about 7 g to about 30 g of liquid.

Processor 22 will typically comprise a programmable electronic microprocessor embodying machine readable computer code or programming instructions for implementing one or more of the treatment methods described herein. The microprocessor will typically include or be coupled to a memory (such as a non-volatile memory, a flash memory, a read-only memory ("ROM"), a random access memory ("RAM"), or the like) storing the computer code and data to be used thereby, and/or a recording media (including a magnetic recording media such as a hard disk, a floppy disk, or the like; or an optical recording media such as a CD or DVD) may be provided. Suitable interface devices (such as digital-to-analog or analog-to-digital converters, or the like) and input/output devices (such as USB or serial I/O ports, wireless communication cards, graphical display cards, and the like) may also be provided. A wide variety of commercially available or specialized processor structures may be used in different embodiments, and suitable processors may make use of a wide variety of combinations of hardware and/or hardware/software combinations. For example, processor 22 may be integrated on a single processor board and may run a single program or may make use of a plurality of boards running a number of different program modules in a wide variety of alternative distributed data processing or code architectures.

Figure 2:
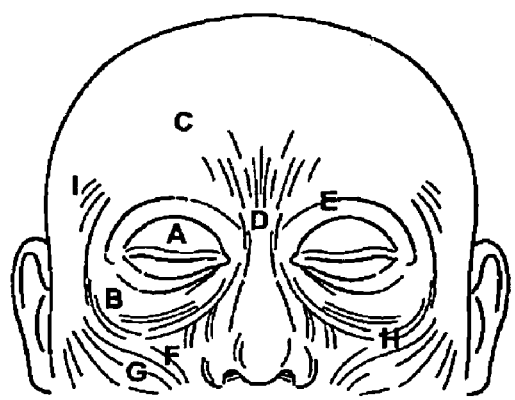
Figure 2M:
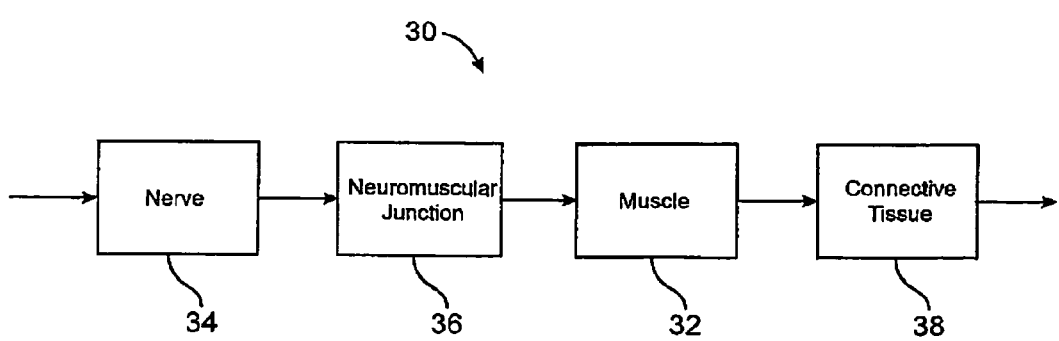
FIG. 2M is a functional block diagram graphically illustrating tissue components included in a contractile chain.
Figure 2A:
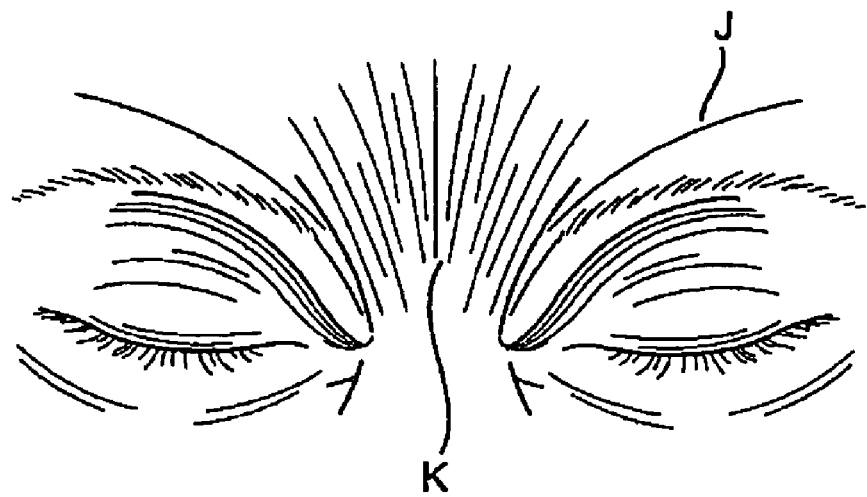
Figure 2B:
Figure 2H:
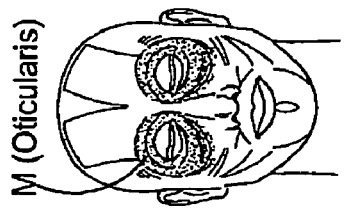
Figure 2H:
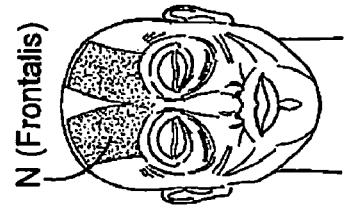
Figure 2H:
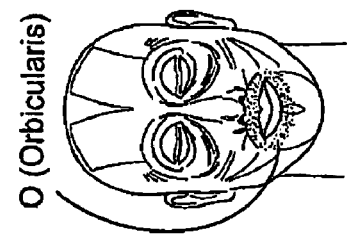
Figure 2H:
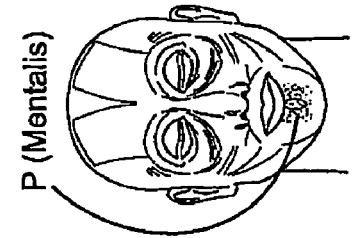
Figure 2H:
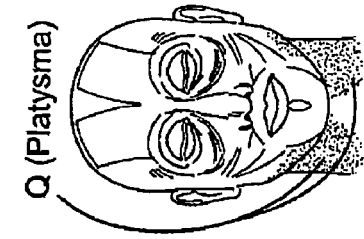
Figure 2H:
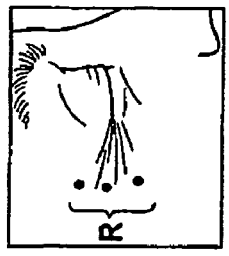
Figure 2I:
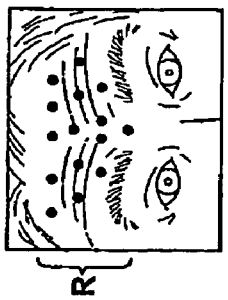
Figure 2J:
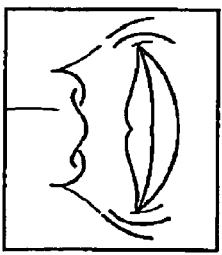

Referring now to FIGS. 2 through 2M, subdermal cryogenic remodeling of tissues for alleviation of lines and wrinkles will find particular applications for skin surface regions of the face and neck, with procedures optionally being performed so as to alter contractile function of muscles A-I in the upper one-third of the face as shown in FIG. 2. Treatments may be performed so as to alleviate frown lines, lines or wrinkles between the eyes, crow's feet, horizontal lines in the forehead, neck, wrinkles around the mouth, chin, and the like. Many of these cosmetic defects may be treated by targeting and/or inactivating tissues such as the corrugator and/or procerus muscles. More specifically, as seen in FIGS. 2A and 2B, movement of the facial muscles can cause the skin to crease, for example, with contraction of corrugator muscle J and/or proceurs muscle K leading to creases between the brows L, which may be clinically referred to as glabellar lines. Additional treatment locations, muscles M-Q whose contractile function may be targeted, related lines or wrinkles, and treatment patterns R are illustrated in FIGS. 2C-2L.

Figure 2K:
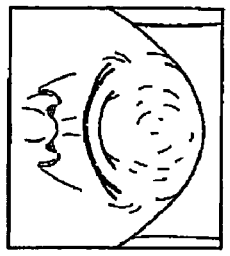
Figure 2L:

Regarding the specific muscles and tissue structures identified in FIG. 2, treatments may be directed towards one or more of levator palpebrae superioris A, orbicularis oculi B, frontalis C, levator labii D, corrugator E, zygomaticus minor F, zygomaticus major G, buccinator H, and/or temporalis I. Treatments targeting contraction of oticularis M of FIG. 2C may help decrease crow's feet wrinkles of FIG. 2H, optionally using a treatment pattern R. Treatments altering the function of Frontalis N of FIG. 2D may alleviate the wrinkles of FIG. 2I, while altering functioning of Orbicularis O of FIG. 2E may alleviate the wrinkles shown in FIG. 2J. Wrinkles of the chin as shown in FIG. 2K may be mitigated by treatment of Mentalis P and neck wrinkles such as those of FIG. 2L may be improved by treatments of platysma Q, as seen in FIG. 2G. Treatment patterns R for improvement of these and other cosmetic defects may correspond to or be derived from known treatments (such as patterns for injections of BOTOX® or the like), may be determined by anatomical analysis using the desired physiological effects, by animal or clinical studies, or the like.

Target muscles for contraction inhibition so as to alleviate wrinkles and the like may often include the glabellar and procerus complex including, but not limited to, the corrugator procerus, orbicularis oculi, depressor, supercilli, and frontalis. Other muscle groups of the facial region may also be contraction-inhibited, such as the nasalis, orbicularis oris, buccinator, depressor anguli oris, quadratus labii superioris and inferioris, zygomaticus, maxillae, platysma, and mentalis. Contraction of these and/or other muscles may be inhibited by targeting associated nerve tissues, connective tissues, nerve/muscle interface, blood supply, and/or at least a portion of tissues of one or more of these muscles themselves. Preferred wrinkle alleviation treatments may alter functioning of muscles including one or more of, but not limited to, frontalis pars medialis, frontalis pars lateralis, corrugator supercilii, procerus, depressor supercilii, levator palpebrae superioris, orbicularis oculi pars orbitalis, orbicularis oculi pars palpebralis, levator labii superioris alaquae nasi, levator labii superioris, zygomaticus minor, zygomaticus major, levator anguli oris (a.k.a. caninus), buccinator, depressor anguli oris (a.k.a. triangularis), depressor labii inferioris, mentalis, incisivii labii superioris, incisivii labii inferioris, risorius, platysma, orbicularis oris, masseter, temporalis, internal pterygoid, digastric, nasalis, maxillae, quadratus labii superioris and inferioris.

In many embodiments, remodeling a tissue included in a contractile function chain 30 will effect a desired change in a composition of the treated tissue and/or a change in its behavior which is sufficient to mitigate wrinkles of the skin associated with contraction of a muscle 32, as illustrated in FIG. 2M. While this may involve a treatment of the tissues of muscle 32 directly, treatments may also target nerve tissues 34, neuromuscular junction tissues 36, connective tissues 38, and the like. Still further tissues may directly receive the treatment, for example, with treatments being directed to tissues of selected blood vessels so as to induce hypoxia in muscle 32 or the like. Regardless of the specific component of contractile chain 30 which is treated, the treatment will preferably inhibit contraction of the muscle 32 which would otherwise form wrinkles or lines in the exposed skin surface overlying that muscle.

A variety of specific tissue remodeling treatments mechanisms targeting of one or more components of contractile chain 30 may be employed so as to inhibit lines or wrinkles. For example, ablation of muscle cells/tissues, or the associated nerves (optionally being a component thereof integral to nerve function such as a myelin sheath or the like), or the nerve endings or neuromuscular junction (which generally forms the interface between the nerves and the muscles) may be sufficient to inhibit muscular contraction. Such ablation may result in a short-term, long-term or permanent inactivation of the muscle. Other long-lasting or permanent treatments may involve inducing apoptosis, typically at temperatures which are not as severe as ablation temperatures, but which remodel the tissue behavior with long term changes in the cellular life and/or proliferation cycles. Specific remodeling mechanisms so as to change the function of the muscle in a desired way or for a desired time may be induced by appropriate therapeutic dosages of the treatment modalities described herein, for example so as to induce cell death (apoptotic or necrotic), embolization of blood supply, or the like. Alternative remodeling mechanisms which may be shorter in effect may include stunning of one or more component of contractile chain 30, inactivation of one or more component, or the like. Remodeling treatments which effectively block the release of or response to chemicals (such as but not limited to acetylcholine) along the contractile chain 30 may be sufficient to inhibit muscular contraction in response to signals transmitted along the neural pathways, either temporarily or permanently, and may also be employed.

Muscular movement is generally controlled by stimulation of a nerve. The motor unit of the neuromuscular system contains three components: motor neuron (spine), axon (spine to motor endplate), and innervated muscle fibers (endplate to muscle). Treatments directed to one or more of these tissues may be employed.

When treatments are intended to inhibit muscle contraction, the treatment may be determined at least in part by the type of muscle being treated (skeletal (striated) or smooth (not striated)). For example, skeletal muscle may have muscle fibers that are innervated by motor neuron, with a single neuromuscular junction lying along a midpoint of muscle fibers, and a single muscle fiber within a motor unit supplied by a single motor neuron and its axon. Each muscle receives one or more nerves of supply, and the nerve generally enters deep into the muscle surface near its origin where the muscle is relatively immobile. Blood vessels typically accompany the nerve to enter the muscle at the neurovascular hilum. Each nerve contains motor and sensory fibers, motor endplates, vascular smooth muscle cells, and various sensory endings and endings in fascia. When the nerve enters the muscle, it breaks off into a plexus running into the various layers of muscle epimysium, perimysium, endomysium each terminating in several branches joining a muscle fiber at the motor endplate. Remodeling of one or more of these tissues may be sufficient to temporarily or permanently inhibit muscle contraction.

Embodiments of the invention may interrupt or disable nerve impulses by disrupting conductivity by eliminating or decreasing charge differences across plasma membranes, either mechanically or chemically; by destroying Schwann cells that insulate the axonal processes speeding up impulse conduction; and/or by repeated injury/healing cycles timed to limited capacity for neuron regeneration.

Immobilization of muscle by disabling any one or a specified combination of components of the connective tissue matrix, either temporarily or permanently, may also be employed. Treatments targeting connective tissues, such as the fibroblasts, myofibroblasts (which may be responsible for contractility of granulation tissue in healing), collagen, reticulin, elastin, or the like of aponeurotic or tendinous attachment of muscles to bone, fascia, ligaments, or the like may also be advantageous, and the remodeling form and/or treatment dosage may be selected in response to the condition being treated (for example, when primarily treating cellulite dimples rather than primarily treating contraction-induced lines or wrinkles). Treatments of the superficial fascia just beneath the skin may also be employed. To achieve a loss of elasticity in fibrous connective tissue during treatment of cellulite, temperature may be varied to achieve temporary or permanent changes to the morphology of the collagen and elastin matrix contained within that tissue.

Along with treating of the target tissue using probe 26, it will often be desirable to inhibit injury to collateral tissues underlying and adjacent to the target tissues, and particularly to the tissues along the skin surface overlying the target tissues. Injury to any desired tissue (blood vessels, nerves, etc.)

may be inhibited, particularly if that tissue is determined to not be targeted in a particular therapy. As illustrated in FIGS. 1A and 1B, a distally oriented applicator 28 adjacent in the distal end 14 of housing 16 may apply energy and/or a material along the skin surface adjacent probe 26 so as to protect the surface tissues from the treatment temperatures. Applicator 28 may, for example, be oriented to engage tissues along the skin surface when the probe 26 is inserted therethrough, the applicator heating the skin surface to prevent injury from the cooling probe. Heating may be provided by a resistive heater or the like, and heat may be transferred to the tissue-penetrating probe body from applicator 28 so as to inhibit injury from the proximal portion of the probe to the adjacent skin tissues. Other embodiments may apply a heated cryoprotectant material above or below the skin surface.

So as to protect adjacent tissues from injury, it may also be advantageous to meter the cooling fluid (such as the liquid $N_2O$) in thermal communication with probe 26 so as to minimize the overflow during treatment times. The amount of liquid $N_2O$ or mass flow rate flowing into a needle probe may be a function of pressure of fluid from fluid source 18, a fluid tube inlet diameter, an internal pressure within the needle, and the quality of the $N_2O$. The amount of liquid $N_2O$ desired to operate a needle probe may be a function on the desired temperature difference between the needle and tissue, which may change over time. Outgoing gas temperatures from the needle probe may change the quality of the incoming $N_2O$ flowing into the needle. Hence, as a result of the dynamic flow requirements, it may be difficult to precisely meter only the amount of desired $N_2O$.

Figure 3:
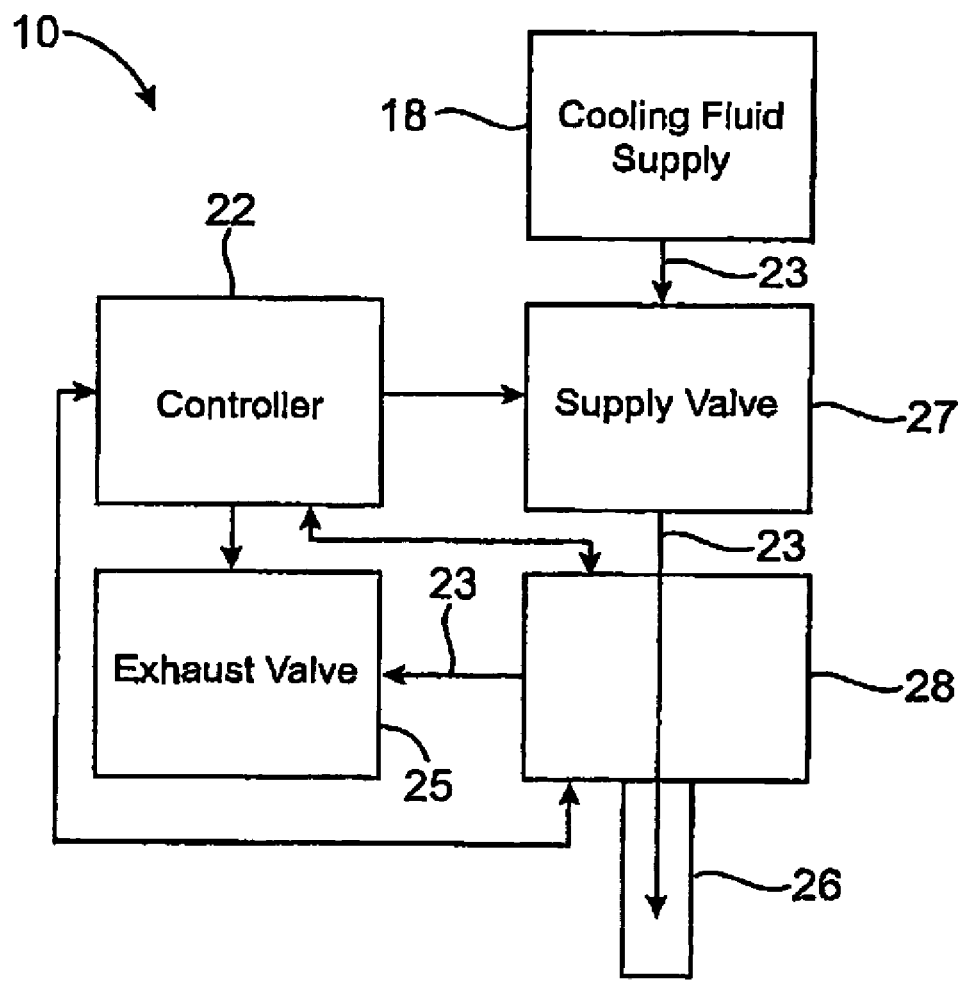
FIG. 3 is a block diagram schematically illustrating functional components of the self-contained probe of FIG. 1A.

Referring now to FIG. 3, a cooling fluid path 23 generally extends from fluid supply 18 to tissue penetrating probe 26, and from the probe to an exhaust (often via exhaust valve 25). A supply valve 27 will often be disposed along fluid path 23 to help control any cooling fluid overflow condition, with the supply valve typically comprising a solenoid or other valve controlled by signals from controller circuit 22. Controller 22 may also provide control signals to exhaust valve 25 in response to temperature or cooling fluid pressure signals, typcially so as to control a temperature of probe 26 and/or a pressure of the cooling fluid therein (or adjacent thereto). Similarly, controller 28 may also control operation of applicator 28, such as by varying electrical energy supplied to a resistive heater in response to a temperature of a temperature-engaging surface of the probe or a temperature of the engaged skin or the like. Controller 22 may transmit signals for other applicators so as to control a flow of fluid from the applicator, for example, by energizing a pump, actuating a valve, or the like.

To control any overflow of cooling fluid into or through probe 26, supply valve 27 along cooling fluid path 23 between fluid supply 18 and the probe 26 may be pulsed so as to allow sufficient flow during different portions of the treatment.

TABLE 1

EXAMPLE OF A 20 SECOND TREATMENT

| Time | Valve Position | Duration | |
|---|---|---|---|
| 0-5 seconds | Open | 5 | seconds |
| 5-7 | Closed | 2 | |
| 7-11 | Open | 4 | |
| 11-13 | Closed | 2 | |
| 13-16 | Open | 3 | |
| 16-18 | Closed | 2 | |
| 18-20 | Open | 2 | |

Table 1 shows an exemplary operation timing for valve 27. During the portions of the treatment when the valve is closed, refrigerant may continue to flow into probe 26, although at a reduced pressure and correspondingly reduced flow rate. The pressure may decay by a rate determined by the volume of the refrigerant fluid path coupling valve 27 to probe 26 (and/or to tube 58 in FIG. 5B). As shown in this example, the proportion of valve open or flow time may be reduced in later stages of the treatment (for example, after more than about 5 seconds of treatment) to match the smaller desired flows. Different probes or probe arrays having different numbers of probes, different lengths, and the like may be mechanically or electronically coded to provide signals to controller 22 so that the controller delivers appropriate on/off (or other modulated) valve timing. Each individual probe may be experimentally characterized to determine appropriate valve timing or other modulation so as limit or avoid refrigerant overflow conditions.

Figure 3A:
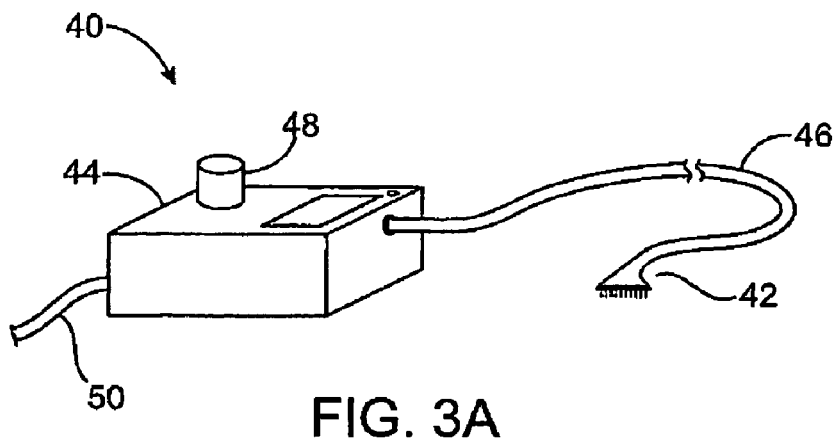
FIG. 3A is a perspective view schematically illustrating another embodiment of a subdermal cryogenic remodeling system having a distal probe handpiece coupled to a proximal housing by a flexible body.

Referring now to FIG. 3A, an alternative subdermal cryogenic remodeling system 40 includes a distal probe handpiece 42 coupled to a proximal controller housing 44 by a flexible body 46. Housing 44 includes a replaceable cooling fluid cartridge 48, with the exemplary cartridge again containing liquid $N_2O$ and a connector for electrical power 50. Housing 44 also includes or contains a user interface for accepting inputs from the system user into a processor contained within the housing, and for outputting parameters regarding the state of the system, the progress of treatment, tissue and/or treatment parameters, and the like.

Figure 3B:
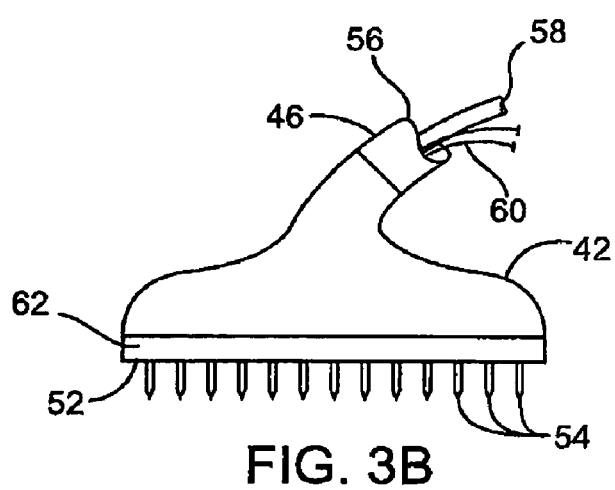
FIG. 3B is a side view schematically illustrating the distal handpiece of the system of FIG. 3A, showing a probe body with a plurality of tissue-penetrating probes extending therefrom.

Referring now to FIGS. 3A and 3B, probe handpiece 42 generally extends distally from flexible probe body 46 to a distal tissue engaging surface 52. A plurality of tissue-penetrating needle probes 54 extend distally from tissue engaging surface 52, with the needle probes being cooled by cryogenic cooling fluid from fluid source 48. Flexible body 46 may include a lumen 56 through which the vaporized cryogenic cooling fluid returns from thermal contact with probes 54 to housing 44, with the housing 44, handpiece 42, or flexible probe body 46 including a valve for regulating pressure of the exhaust gases so as to control a treatment temperature under the direction of the processor within the housing. A cooling fluid supply lumen 58 may also be included within flexible body 46 for transmitting the liquid cooling fluid to probes 54. Electrical power for handpiece 42 may be provided form housing 44 by electrical conductors 60.

In the embodiment of FIG. 3B, handpiece 42 includes an applicator in the form of a heated pad 62, the distal surface of the heating pad comprising the tissue engaging surface 52. In general, the temperature of the skin engaging surface of the probe may be between about 37° C. and about 90° C., with warmed probe tissue engaging surfaces having a temperature from about 45° C. to about 90° C. before skin contact, depending of the physical properties of the probe surface, so that the skin has a temperature from about 37° C. to about 45° C. during treatment. Probe surfaces formed on thermally conductive materials (for example, metals such as copper, aluminum, or the like) may be heated so as to have temperatures closer to 45° C. prior to contact with the skin, while non-heat conductive materials (often including polymers such as a silicone or a PTFE such as a Teflon™ material) may be heated to have temperatures closer to 90° C. before contact. Other factors which may influence the desired probe skin engaging surface temperature before skin contact include the mass of the underlying probe structure, the location of the heater, and the like. Independent of the initial probe temperature at contact, the maximum desired temperature that the skin reaches may be about 45° C. To protect the skin and/or surrounding tissue, the probes described here may be provided with applicators which apply heat energy, materials, or the like to inhibit injury along the skin surface or other tissue not targeted by a particular therapeutic treatment.

The application of energy can heat collateral tissues near tissues targeted for application of cooling-based remodeling, such as to control temperatures at the inner and/or outer surfaces of the skin, in the surrounding tissues, or the like. This may be achieved with energy sources and/or by applying temperature managed fluid. In FIG. 3B, the exemplary applicator comprises, for example, heating pad 62 of stainless steel or the like. Heating of the applicator may be provided by a resistive heater structure powered by conductors 60 under the direction of the processor circuitry contained within controller housing 44.

Along with circuitry for controlling the heater of the tissue engaging probe surface, the processor circuitry within controller housing 44 will provide on/off or metered flow control for the $N_2O$ (as well as pressure regulation), a timer for applying and/or varying heating, cooling, the application of cryoprotectants or other materials, or the like. A wide variety of pre-cooling, during-cooling, and/or post-cooling collateral tissue inhibiting treatment regiments may be employed so as to allow the target tissues to be cooled to the desired treatment temperatures for the desired treatment times with appropriate rates of change in the temperature to provide the desired remodeling effect, while collateral tissues along the skin surface or the like are maintained at injury inhibiting temperatures.

Figure 3C:
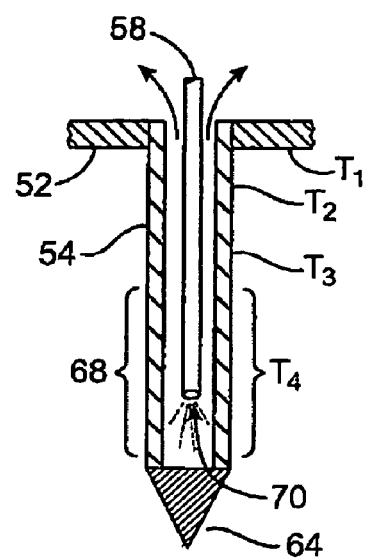
FIG. 3C is a cross-sectional view showing the structure of the tissue-penetrating probes of the probe body of FIG. 3B.

Referring now to FIGS. 3B and 3C, the cooling and structure of tissue-penetrating probes 54 can be seen in more detail. Each probe again comprises a 30 g 0.012 inch outer diameter tube or needle having a sharpened distal end 64. A temperature along the skin-engaging surface 52 (and hence adjacent the proximal end of tissue-penetrating probe 54) $T_1$ may be warmer than skin temperature, typically being warmer than 37°, and in the exemplary embodiment being about 50° C. A distal portion of the tissue-penetrating probe 54 for engaging a target tissue will have a temperature $T_4$ that is generally less than 10° C., often being 0° C. or less, and in many embodiments being −5° C. or less, in some embodiments being −15° C. or less, or even −25° C. or less so as to provide a sufficient tissue volume in the desired tissue temperature range. The exemplary penetrating needle 54 shown in FIG. 3C may have a distal portion 68 with a length of over about 1 mm, optionally being about 3 mm in length, and may be cooled to provide a probe outer surface treatment temperature $T_4$ of about −40° C.

A portion of the cooling fluid directed to handpiece 42 is transmitted along a cooling fluid lumen 58 within the handpiece (from a manifold or the like, or optionally with each tissue-penetrating probe having an associated lumen extending through flexible body 46), with at least a portion of the cooling fluid flowing as a liquid from a cooling fluid inlet 70 into the interior of tissue-penetrating probe 54. The cooling fluid vaporizes within probe 54, and the exhaust gases are vented proximally into an interior of handpiece 42, then through lumen 56 of flexible body 46.

Referring still to FIG. 3C, distal portion 68 of probe 54 will generally contain a mixture of cooling fluid in its liquid form with cooling fluid in its gaseous form. As the vaporization or boiling temperature of a fluid generally varies with pressure, if the pressure within distal portion 68 is relatively constant, the probe surface treatment temperature $T_4$ along distal portion 68 will be relatively constant and can be controlled by varying the pressure within probe 54 and/or handpiece 42.

The outer probe surface temperatures $T_2$, $T_3$ between distal portion 68 and skin engaging surface 52 will typically be somewhat warmer than the target tissue probe treatment temperature $T_4$, particularly when the skin engaging surface 52 is heated. As the mix of liquid and gas cooling fluid flows proximally within tissue-penetrating probe 54 and, the liquid may eventually fully vaporize allowing the gas to increase in temperature. Hence, the outer probe surface may warm gradually as you move proximally from the distal portion 68. Even where the liquid is not fully vaporized, heat may be transmitted from heated pad 62 distally along the probe body. In the exemplary embodiment, the intermediate temperature $T_2$ may be about 0° C., with the temperature $T_3$ being about −20° C.

Figure 4A:
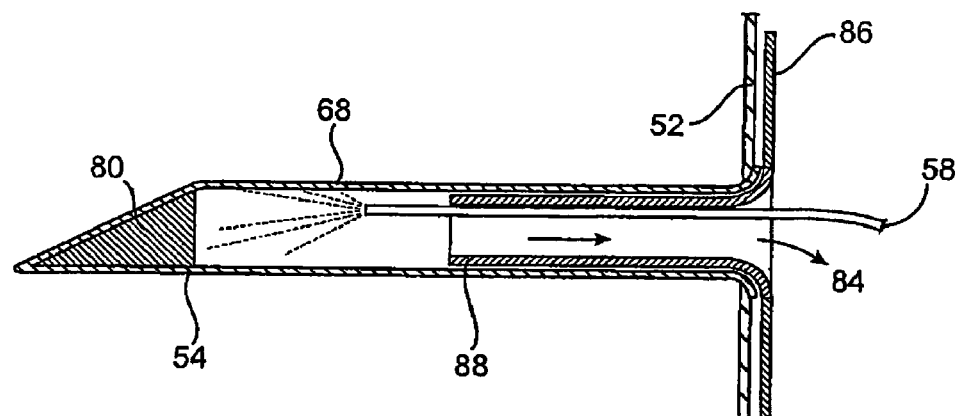
FIG. 4A is a cross-sectional view of an alternative tissue-penetrating probe having insulation along a proximal portion of the probe so as to inhibit cooling adjacent in the probe body.
Figure 4B:
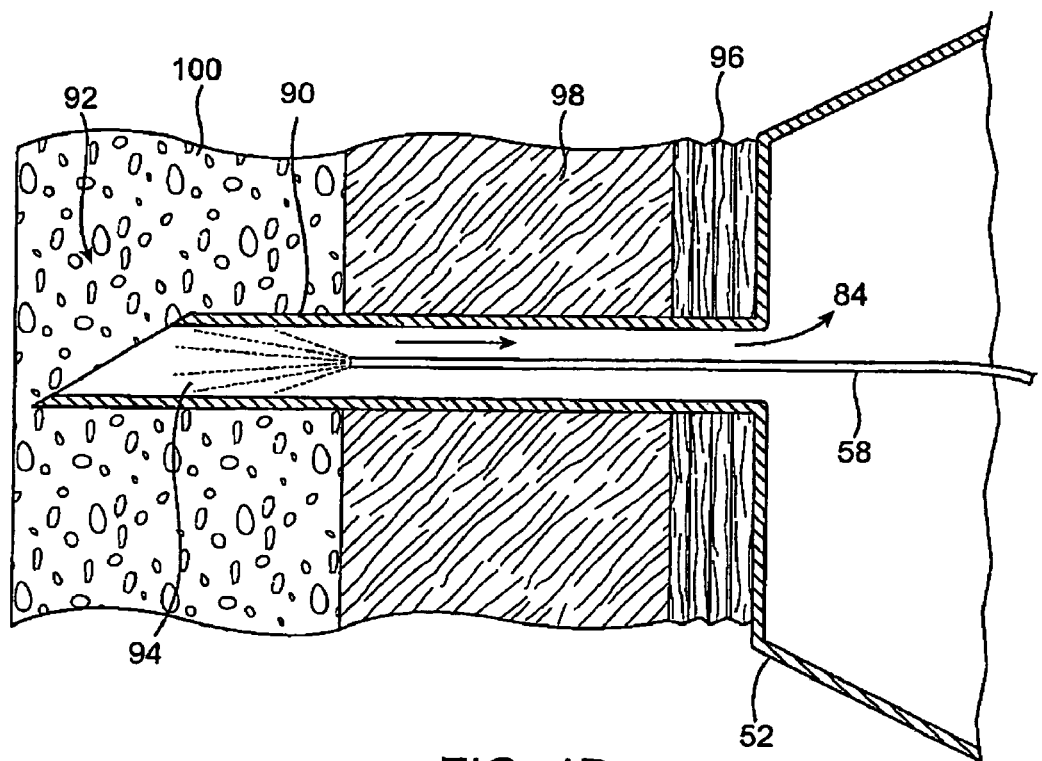
FIG. 4B is a cross-sectional view showing a still further alternative tissue-penetrating cryogenic probe having an open distal end, along with a method for its use.

Referring now to FIGS. 4A and 4B alternative mechanisms may also be provided to inhibit injury along the skin surface, including thermally insulating at least a portion of the tissue-penetrating probe or skin-engaging surface of the probe handpiece. Tissue-penetrating probe 54 here again comprises a 30 g stainless steel tube having an outer diameter of about 0.012 inches and an inner diameter of about 0.006 inches, with a closed distal end 80. Liquid $N_2O$ is again introduced through cooling fluid supply lumen 58, with vaporized gasses $N_2O$ 84 being exhausted proximally through the inner lumen of tissue-penetrating probe 54. Optionally, closed end 80 may limit the advance of cooling fluid within tissue-penetrating probe 54 so as to inhibit cooling of collateral tissues disposed distally of the target tissues, with the closed distal end optionally having a resistive heater, an insulating material, a tissue heating electrode, a cryoprotectant delivering port, or some other distal tissue protection applicator.

In the embodiment of FIG. 4A, insulation 86 is provided between the cooling fluid flowing within the probe handpiece and the skin engaging surface 52 to protect the epidermis from thermal coupling with any overflow liquid $N_2O$ or the like. Additionally, an insulation layer or sleeve 88 disposed between an outer surface of probe 54 and the cooling fluid within probe 54 limits thermal cooling by the cooling fluid proximally of the distal target tissue-engaging portion 68.

Optionally, direct cooling of the target tissue through contact between the cooling fluid and tissue may be provided, as illustrated in FIG. 4B. In this embodiment, a probe 90 has an open end 92. Liquid $N_2O$ 94 (or some other cryogenic cooling fluid) is directed from cooling fluid lumen 58 toward open end 92, with vaporized exhaust gases 84 again returning proximally.

When probe 90 is inserted through the layers of the epidermis 96 and dermis 98 so that the distal portion of the probe is within a target tissue 100, the skin-engaging surface 52 of the probe handpiece is pushed firmly against the skin, thereby providing pressure to the dermal layers in the target tissue. The target tissue 100 partially invaginates in the needle lumen of probe 90, blocking the distal end closed. The combined compression of the target tissue and invagination contain the nitrous oxide $N_2O$ (or other cooling fluid) within the needle probe 90.

Figure 5A:
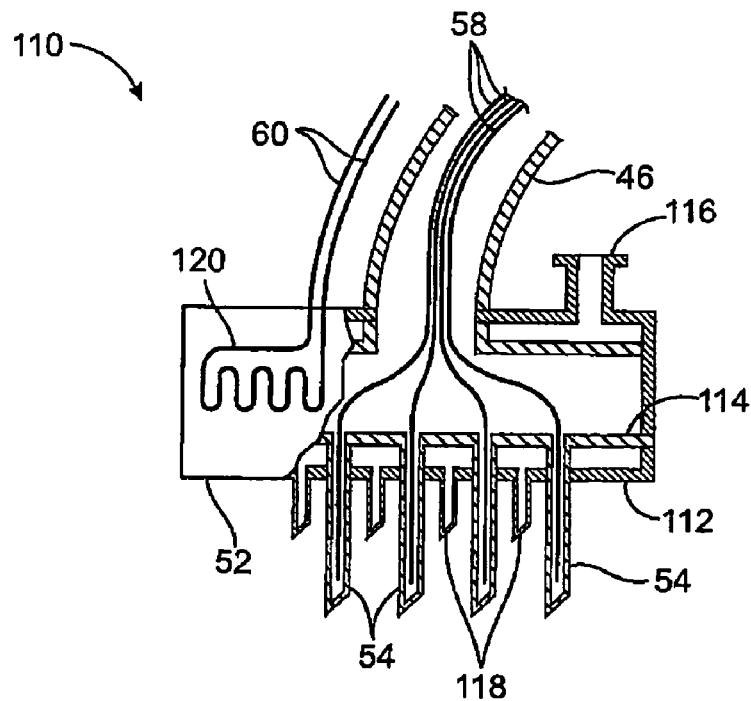
FIGS. 5A and 5B schematically illustrate cross-sectional views of an alternative treatment probe handpiece having a plurality of tissue-penetrating cooling probes, and also having an applicator for applying energy and/or an injectable material to inhibit cooling injury between the target tissues and the skin surface.
Figure 5B:
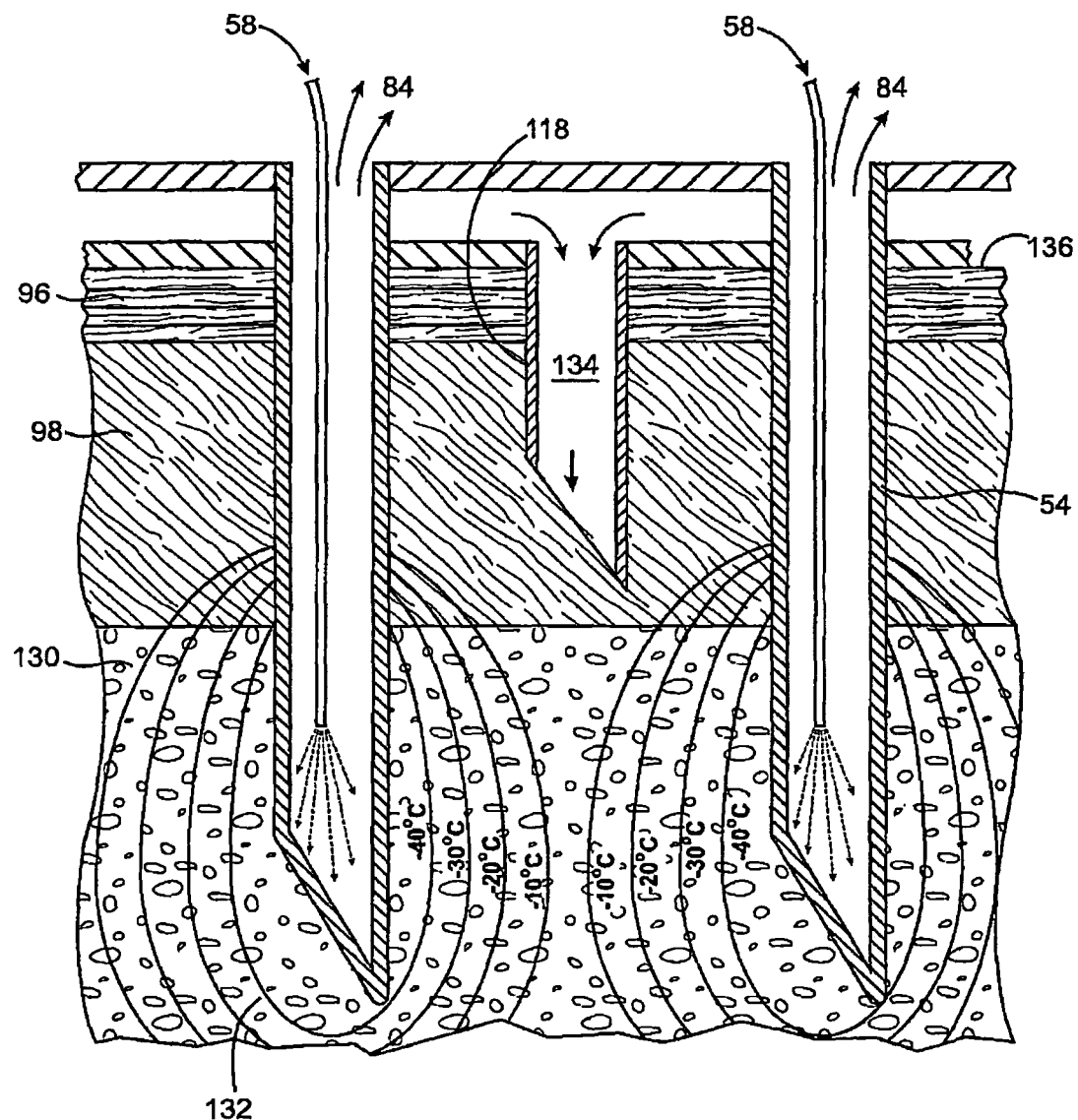

Referring now to FIGS. 5A and 5B, alternative probe handpiece 110 has an applicator 112 that applies both heating and a cryoprotectant compound to the tissues disposed between the skin surface and the target tissues to inhibit collateral tissue damage.

The application of one or more cryoprotectant compounds (such as dimethyl sulfoxide, DMSO, and/or the like) to the inner and/or outer surface of the skin, into the collateral tissue, or the like, with or without heating of the compounds, may inhibit collateral tissue damage. Probe handpiece 110 may also be used to inject warmed biocompatible fluids such as saline into the dermal layers above the target tissue so as to inhibit collateral tissue damage. DMSO or other cryoprotectants or biocompatible solvents may be applied to the epidermis and/or dermis before or during treatment. A variety of materials may be used, including DMSO cocktails, propylene glycol and the like.

Addressing the structure shown in FIGS. 5A and 5B, handpiece 110 includes an outer housing 112 and an inner chamber defined by an inner housing 114, the inner housing optionally comprising (for example) a stainless steel tube having an outer diameter of 0.14 inches and an inner diameter of 0.12 inches. The outer housing 112 in part defines an applicator for applying both heat and a cryoprotectant material to dermal tissues, the inner and outer housing together defining a space therebetween for a passage of an infusion fluid from an input port 116 (such as a Luer fitting) to a plurality of infusion and needles 118. In the exemplary embodiment, the outer housing 112 comprises a stainless steel tubing having an outer diameter of 0.20 inches and an inner diameter of 0.18 inches. A heater 120 is thermally coupled to the infusion fluid between the inner and outer housings, warming the fluid infused by infusions needles 118 and providing skin engaging surface 52 with a temperature of about 45° C.

The tissue-penetrating needle cooling probes 54 may comprise 30 g needles with blocked distal ends and having a length of about 3 mm. Fluid infusion needles 118 may comprise 30 g needles having a length of about 1.5 mm. In general, the spacing between tissue-penetrating cooling treatment probes 54 may be between about ¼ mm and 2 mm, preferably having a needle-to-needle spacing of between about ½ mm and 1 mm, ideally being about ½ mm. Where fluid infusion needles 118 are provided, they may be interspersed between at least some of the adjacent cooling treatment probes 54 and/or around a perimeter of the cooling treatment probes to limit the lateral spread of cooling.

As illustrated in FIG. 5B, the distal portion of a multi-needle probe handpiece with saline or other fluid infusion may again have needle probes 54 extending through the dermis 98 and epidermis 96 to a treatment zone, here in the hypodermis 130. Treatment zones may generally be defined by the temperature profiles 132 in the cooled tissues adjacent the distal portion of the cryogenic cooling needle probes 54. Warm saline 134 infused into the dermis 98 and/or epidermis 96 by infusion needles 118 may limit collateral injury to these tissues between treatment zones 132 and the skin surface 136.

As can be understood with reference to the temperature profiles illustrated in FIG. 5B, treatment zones 132 may provide desired temperatures in selected volumes or patterns of the target tissue, with adjacent target tissue regions being below or above the target treatment temperatures. As can be understood with reference to FIGS. 6A and 6B, applying cooling from a tissue-penetrating cryogenic probe in which cooling is applied primarily or entirely through a distal portion of the probe can also help limit cooling injury to the tissues adjacent the skin surface. Advantageously, the temperature profiles can, to a significant extent, be determined by selecting a probe surface temperature, a cooling treatment time, a needle-needle spacing, a probe and insulation geometry, and the like.

Figure 6A:
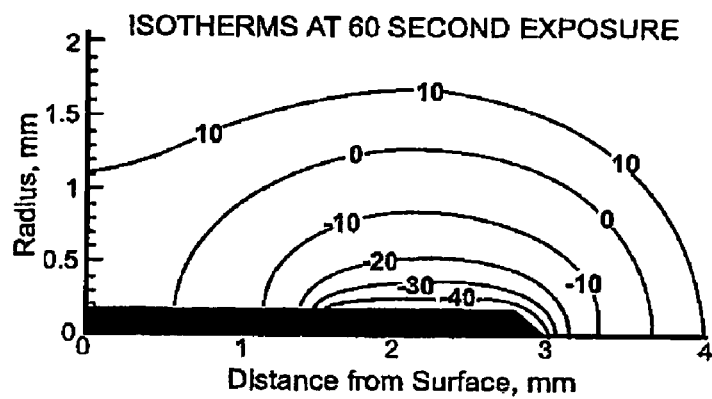
FIGS. 6A and 6B graphically illustrate temperature distributions measured from a center line of a tissue-penetrating cryogenic cooling probe.
Figure 6B:
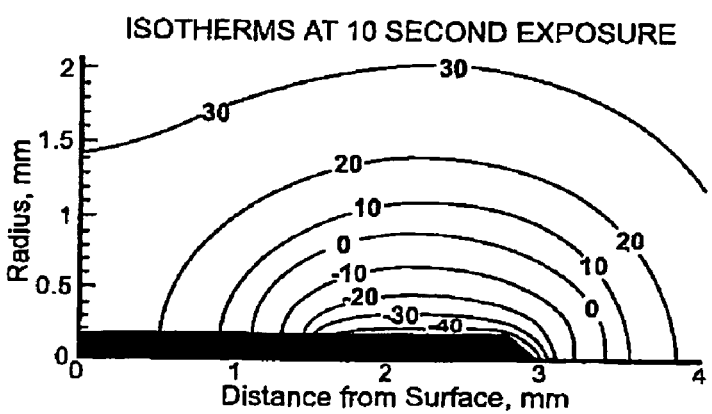

FIG. 6A shows isotherms of tissues, as measured from a center of a tissue-penetrating probe, after 60 seconds of exposure to cooling at −50° C. of probe surface temperature. The tissues along the skin surface reach a minimum temperature of below 10° C. and above 0° C. A similar plot of tissue temperature isotherms after 10 seconds of cooling exposure provides surface tissue temperatures above 20° C., as illustrated in FIG. 6B. Application of energy or suitable materials to collateral tissues may further tailor the shape of the tissue remodeling effect. Alternatively, damage to the tissues along the skin surface and the like may be limited by effecting the desired cosmetic result utilizing temperature ranges and/or times which inhibit damage to the collateral tissues.

As indicated above, a variety of methods may be used to protect the skin at the epidermal and/or the endodermal layers. For example, a delivery probe with multiple temperature zones may be used, the zones optionally corresponding to probe materials and/or insulation. In some embodiments, insulation (optionally segmented) may be built into delivery device; injection of saline or other heated biocompatible fluid may be provided; injection of biocompatible cryoprotectant may be provided; and/or the application of energy may be provided to limit collateral tissue damage.

Still further alternative mechanisms may be used to limit collateral tissue damage, optionally by enhancing the effects of cooling or other remodeling upon the target tissues. In some embodiments, it may be advantageous to enhance sub-thermal ice formation and/or heat conduction. Fat has insulation properties, and saline can be 3× as conductive as fat, so that adding saline (or other conductive agents) may help with freezing of some target tissues, including adipose tissues. Hence, injection of saline or some other material may enhance thermal conductivity and cooling remodeling efficacy and/or target region control. The injection of such materials to spread remodeling efficacy across a broader anatomical region may be particularly desirable. In some embodiments, saline may be infused by or adjacent to the cooling needles or tissue-penetrating probes 54. The cooling front may preferentially travel through the saline. Below 0° C. or solidification of the saline, the saline may still be approximately three times as conductive of heat as fatty tissues. Injection or other application of compounds may also enhance desired remodeling of the tissue via other mechanisms. For example, application of hypertonic solutions such as saline having sufficient salinity may enhance the effects of cold or heat on target tissues by altering a size of cells, dehydrating cells, and or the like. In some embodiments, application of such hypertonic solutions may effect the desired remodeling of target tissues without application of cold or heat.

Permanent and/or temporary muscular function inhibition may be employed. A temporary effect can be used on a trial basis to avoid long term injuries or undesirable outcomes. A permanent effect may be desirable to minimize cost and avoid repeated treatments. Desired temperature ranges to temporarily and/or permanently disable muscle, as well as protect the skin and surrounding tissues, may be indicated by Table 2 as follows:

TABLE 2

| Temperature | Skin | Muscle/Fat |
|---|---|---|
| 37° C. | baseline | baseline |
| 25° C. | cold sensation | |
| 18° C. | reflex vasodilation of deep blood vessels | |
| 15° C. | cold pain sensation | |
| 12° C. | reduction of spasticity | |
| 10° C. | very cold sensation reduction of chronic oedema Hunting response | |
| 5° C. | pain sensation | |
| 0° C. | freezing point | |
| −1° C. | | Phase transition begins |
| −2° C. | | minimal apoptosis |

TABLE 2-continued

| Temperature | Skin | Muscle/Fat |
|---|---|---|
| −3° C. | | Peak phase transition |
| −5° C. | tissue damage | moderate apoptosis |
| −8° C. | | Completion of phase transition |
| −10° C. | | considerable apoptosis |
| −15° C. | | extensive apoptosis |
| | | mild-moderate necrosis |
| −40° C. | | extensive necrosis |

To overcome the potential for an undesirable outcome, treatments may be administered in a controlled manner, a little at a time over the course of several procedures. Where muscle is concerned, a temporary loss of elasticity through changes in the morphology of the collagen and elastin may be seen with the onset of ice formation. The degree to which there is a loss of movement is likely to increase as a greater percentage of cells are affected. This can be controlled by varying treatment parameters such as times, rates, and temperatures. The lower the temperature, the higher the percentage of cells is that undergo the contraction-inhibiting effect.

In light of the above, and so as to provide cosmetic tissue remodeling with a desired or selected efficacy duration, tissue treatment temperatures may be employed per Table 3 as follows:

TABLE 3

| Cooled Temperature Range | Time Effectiveness | Purpose |
|---|---|---|
| ≧0° C. | Treatment lasts only while the needle is inserted into the target tissue. | Can be used to identify target tissues. |
| From 0° C. to −5° C. | Often lasts days or weeks, and target tissue can repair itself. Embodiments may last hours or days. | Temporary treatment. Can be used to evaluate effectiveness of remodeling treatment on skin surface shape or the like. |
| From −5° C. to −15° C. | Often lasts months to years; and may be permanent. Limited muscle repair. Embodiments may last weeks to months. | Long term, potentially permanent cosmetic benefits. Can be deployed in limited doses over to time to achieve staged impact, controlling outcome and avoiding negative outcome. May be employed as the standard treatment. |
| From −15° C. to −25° C. | Often lasts weeks or months. Muscle may repair itself via satellite cell mobilization. Embodiments may last years. | May result in Mid-term cosmetic benefits, and can be used where permanent effects are not desired or to evaluate outcomes of potentially permanent dosing. Embodiments may provide permanent treatment. |

As can be understood with reference to FIGS. 5B, 6A, and 6B, some tissues may be exposed to temperatures above or below the desired treatment range, and varying effects on tissues may occur, particularly including some necrosis when using colder temperatures.

There is also a window of temperatures where apoptosis can be induced. An apoptotic effect may be temporary, long-term (lasting at least weeks, months, or years) or even permanent. While necrotic effects may be long term or even permanent, apoptosis may actually provide more long-lasting cosmetic benefits than necrosis. Apoptosis may exhibit a non-inflammatory cell death. Without inflammation, normal muscular healing processes may be inhibited. Following many muscular injuries (including many injuries involving necrosis), skeletal muscle satellite cells may be mobilized by inflammation. Without inflammation, such mobilization may be limited or avoided. Apoptotic cell death may reduce muscle mass and/or may interrupt the collagen and elastin connective chain. Temperature ranges that generate a mixture of these apoptosis and necrosis may also provide long-lasting or permanent.

Apoptosis, alternately termed "programmed cell death", is a gene-directed self-destruct mechanism by which cells die without adversely affecting surrounding tissues. It is characterized by a well-ordered sequence of events, including chromatin condensation, nuclear fragmentation, and membrane blebbing. Apoptosis plays a number of roles in the development and regulation of healthy tissue. As part of normal tissue development and differentiation, apoptosis is part of a strategy to select certain cells for survival, thereby sculpting a tissue's specificity. In mature tissue, apoptosis balances cell division to prevent excess tissue growth.

Another role of apoptosis is to ensure that injured or mutated cells do not proliferate. Environmental or physiological stimuli which damage the cell may induce or activate the genetic program for apoptosis. Specifically, injurious external stimuli (such as cold exposure) can activate the genes which drive the apoptotic cascade of events. Apoptosis can be elicited by a physiological stimulus that is not per se harmful and that causes death to only a specific population of cells and various forms of cellular injury, whether induced by immune effector cells, aberrant metabolic processes, chemotherapeutic drugs or temperature shifts, can result in common morphological changes including the formation and shedding of membrane vesicles from the injured cell surfaces, and/or apoptosis.

In other words, normal cells may be genetically programmed with a suicide routine, leading to the term "programmed cell death". This programming can be activated or triggered by non-lethal cold exposure. Alternative mechanisms may also be used to trigger apoptosis, including appropriate chemical or heat exposure as well as hypoxia induced stress by loss of vascular perfusion. Therefore, cryo-treatment and other methods can accurately be described as inducing or triggering apoptosis.

For the reduction of adipose tissue, a permanent effect may be advantageous. Surprisingly, both apoptosis and necrosis may produce long-term or even permanent results in adipose tissues, since fat cells regenerate differently than muscle cells.

Aspects of healing which can be helpful for these treatments include the four phases of healing: inflammation (immediate); substrate (6 hours); repair (5-6 days); and maturation. Return of at least some muscular strength in normal healing typically occurs in 4-6 days after injury, and may peak 14-16 days. Scarring in tendons can cause lengthening, thereby inhibiting contractions of an associated muscle. More, specifically separation injury may result in growth of new tissue to reconnect, resulting in increased length and loss of contractility (and hence a flaccid muscle). Healing can occur through both fibrosis and regeneration of myofibrils. Scar tissue can strangle myofibrils, preventing regeneration. Between muscle ends, scar tissue can elongate resulting in poor contractility. Similarly, any break in a chain of connective tissue can inhibit contractions, including in a ligament or tendon. Ligaments can have an ability to reform, closely approximating the original pre-treatment structure. Like tendon, if ends (of severed injury) don't heal together, elongation can occur leaving it weak. Non-severed injury may effectually be similar to a sutured break which does not elongate.

Figure 7A:
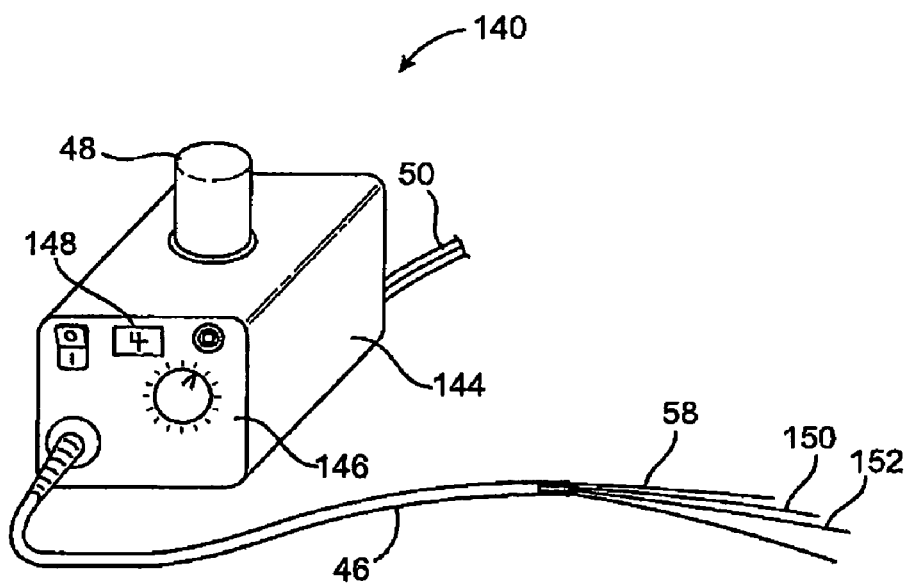
FIGS. 7A and 7B are perspective views schematically illustrating a proximal housing and a distal handle of another subdermal cryogenic remodeling system, respectively.
Figure 7B:
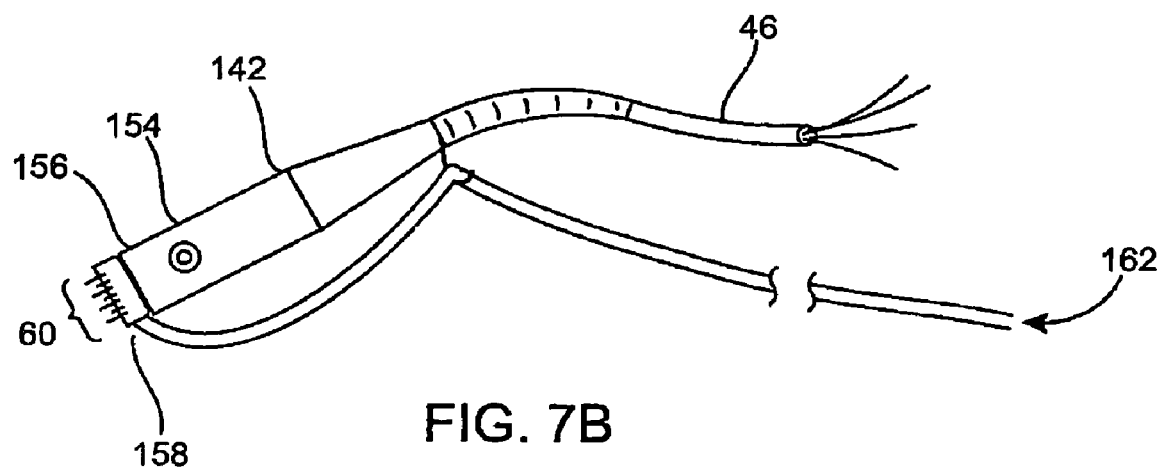

Referring now to FIGS. 7A and 7B a still further alternative system may include a proximal controller housing 140 and/or a probe applicator handpiece 142 as schematically illustrated. In this embodiment, controller housing 144 includes a receptacle for a cooling fluid cartridge 48 with the cooling fluid to cartridge being replaceable and having sufficient cooling fluid for at least a significant portion of a treatment of a single patient. The user interface of controller housing 144 includes a treatment time selector and/or indicator 146 and an indicator 148 which may generally indicate the treatment type or characteristics such as the treatment temperature, treatment efficacy duration, or the like.

Flexible body 46 extending between controller housing 144 and probe handpiece 142 includes a cooling fluid supply lumen 58, along with a thermal couple feedback 150, a heater power on/off switch conductor 152, and the like. Handpiece 142 includes a start button 154, and includes both a proximal housing 156 and a replaceable distal body 158. Body 158 includes an array of needles 160 as described above, and is detachably coupled to proximal body 156 and to a saline or other fluid infusion source 162. The fluid source 162 may comprise a pump, syringe, drip system, or the like and may provide a saline, a cryoprotectant, another biocompatible fluid, or the like. The fluid may be supplied warm from the fluid source 162 or maybe warmed at or adjacent body 158.

Figure 8A:
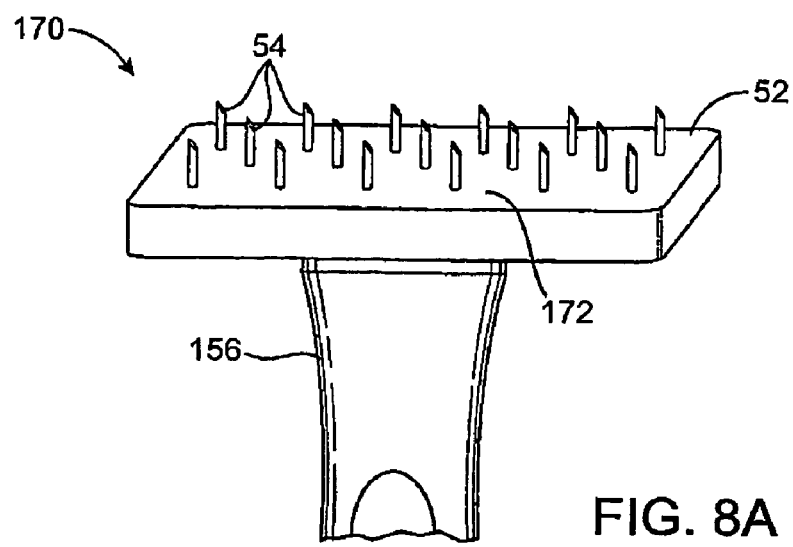
FIGS. 8A-8C illustrate a plurality of alternative treatment handpieces having a variety of different tissue-penetrating cooling probe arrays.
Figure 8B:
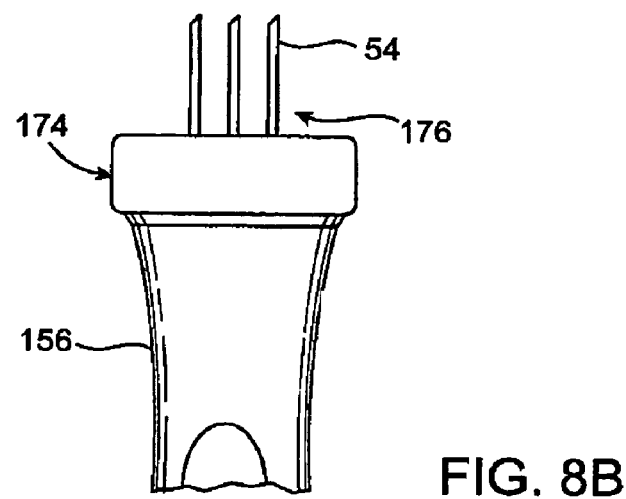
Figure 8C:
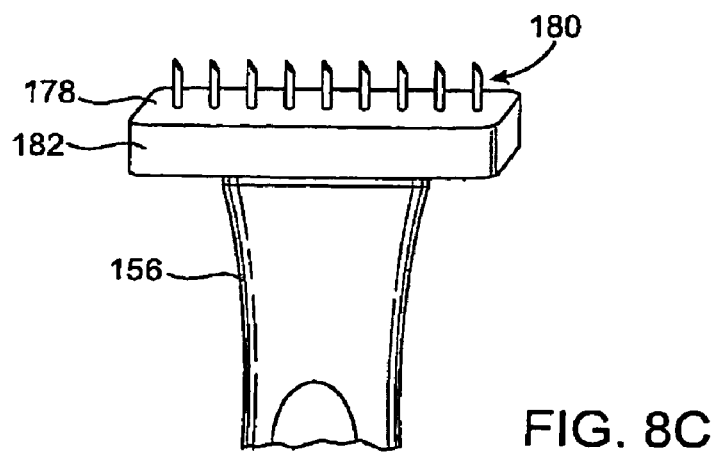

Referring now to FIGS. 8A-8C, a plurality of alternative probe handpiece bodies or heads of differing configurations may be provided. Probe head 170 includes an array of tissue-penetrating probes or needles 54 which are arranged to produced a treatment volume. A thermal sensor 172 on skin engaging surface 52 monitors skin temperature, and may be used to control a skin heater of the probe and/or the cooling treatment.

An alternative probe head 174 shown in FIG. 8B includes long tissue-penetrating probes 54 arranged in a linear array 176, and facilitates treatments along a plane, such as parallel to a bone. A still further alternative probe head 178 similarly includes a needle array 180 are ranged to produce a shallow treatment to plane or line. A probe base 182 can be rigid (for example, being formed of stainless steel) or can be flexible to conform to the engaged skin or tissue surface (i.e., silicon). Resistive heating elements may be provided within probe head base, whether it is rigid or flexible. For example, a resistive heating element inside a silicon probe head base having about 2.5 watts per square inch of surface area may produce surface temperatures of approximately 45° C., suitable for warming a skin surface.

Figure 9:
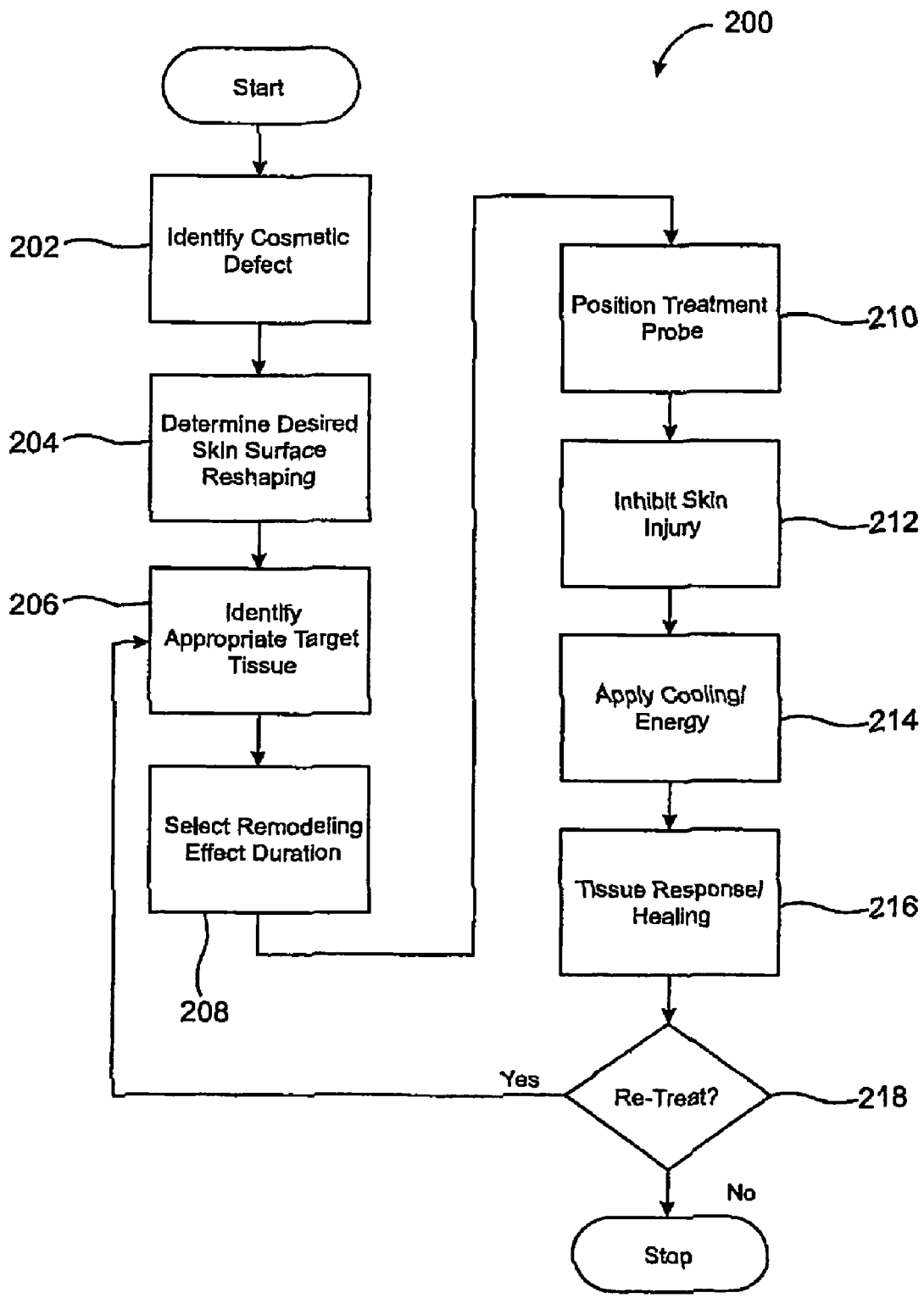
FIG. 9 is a flowchart schematically illustrating a method for cosmetically treating a target tissue disposed below a skin surface using cryogenic cooling so as to reshape the skin surface.

Referring now to FIG. 9, an embodiment of a method 200 for effecting a cosmetic treatment 200 includes identifying a cosmetic defect 202 such as lines, wrinkles, cellulite, fat, or the like. A desired skin surface reshaping is determined 204 which may include the elimination of lines or wrinkles, smoothing of cellulite dimples, reduction of fat, or the like. In many embodiments, it may be desirable to avoid permanently altering a color of the skin surface in effecting such treatments.

An appropriate target tissue is identified 206, such as identifying a nerve, muscle, neuromuscular junction, connective tissue, adipose tissue layer, or the like below the cosmetic defect. A remodeling effect duration 208 may be selected, and the treatment probe positioned 210. Positioning of the treatment probe may, for example, comprise inserting one or more tissue-penetrating probe needles into the target tissue, engaging the skin surface with a skin-engaging surface of a handpiece, and/or the like. Injury to the skin may be inhibited 212, such as by warming the skin surface, infusing a warmed biocompatible fluid such as saline, applying a cryoprotectant such as DMSO, or the like.

Cooling and/or energy (or chemical or vascular embolization) is applied to the target tissue 214 so as to effect the desired remodeling of that tissue. The tissue response and healing 216 may follow immediately after cooling and/or energy (or chemical or vascular embolization) is applied, or may take place over a considerable time (such as when efficacy is achieved through apoptosis or the like). If a short duration or trial treatment was performed to verify the target tissue and treatment effect, retreatment 218 may be performed.

While the exemplary embodiments have been described in some detail for clarity of understanding and by way of example, a number of modifications, changes, and adaptations may be implemented and/or will be obvious to those as skilled in the art. For example, one or more temperature feedback loops may be used to control the treatments, with the tissue temperature optionally being taken at varying tissue levels using (for example) the plurality of thermal couples advanced to varying depths of the tissue using a temperature sensing needle. Hence, the scope of the present invention is limited solely by the independent claims.

What is claimed is:

1. A method for improving a cosmetic appearance of a patient, the patient having a skin surface comprising a region of the face, the method comprising piercing a probe through the skin surface and directing cooling from the probe to a target tissue and cooling the target tissue below the skin surface such that the target tissue is remodeled and the remodeling of the target tissue temporarily inhibits contraction of a muscle so as to reduce the appearance of lines and wrinkles in the face associated with contraction of the muscle.

2. The method of claim 1, wherein the target tissue comprises a muscle of the face, an associated nerve, an associated connective tissue, or an associated nerve/muscle junction.

3. The method of claim 2, wherein the cooling inhibits contraction of a muscle selected from the group consisting of: frontalis pars medialis, frontalis pars lateralis, corrugator supercilii, procerus, depressor supercilii, levator palpebrae superioris, orbicularis oculi pars orbitalis, orbicularis oculi pars palpebralis, levator labii superioris alaquae nasi, levator labii superioris, zygomaticus minor, zygomaticus major, levator anguli oris, buccinator, depressor anguli oris, depressor labii inferioris, mentalis, incisivii labii superioris, incisivii labii inferioris, risorius, platysma, orbicularis oris, masseter, temporalis, internal pterygoid, digastric, nasalis, maxillae, quadratus labii superioris and infenoris.

4. The method of claim 1, further comprising inhibiting cooling-induced injury to the skin surface so as to selectively cool the target tissue.

5. The method of claim 4, wherein cooling-induced injury to the skin surface is inhibited by applying warming energy along the skin surface.

6. The method of claim 5, wherein the energy is applied along the skin surface by engaging the skin surface with an applicator of the probe and heating the skin surface with the applicator during the cooling, of the target tissue.

7. The method of claim 4, wherein cooling-induced injury to the skin surface is inhibited by a cooling injury inhibiting material disposed along the skin surface during the cooling.

8. The method of claim 4, wherein the cooling injury inhibiting material comprises a heated biocompatible fluid or a biocompatible cryoprotectant.

9. The method of claim 4, wherein cooling-induced injury to the skin surface is inhibited by applying a cooling injury enhancing material to the target tissue, the cooling injury enhancing material being separated from the skin surface sufficiently that cooling of the skin surface is limited.

10. The method of claim 4, wherein cooling-induced injury to the skin surface is inhibited sufficiently to avoid permanently altering a color of the skin surface.

11. The method of claim 1, wherein the cooling is performed so as to induce a reduction in tissue mass after removal of the probe from the patient, the cooling-induced reduction in tissue mass providing a desired change in a shape of the skin surface.

12. The method of claim 11, wherein the cooling reduces muscle mass.

13. The method of claim 1, wherein the target tissue is cooled to a temperature in a range from about 10° C. to about −50° C.

14. The method of claim 1, wherein the target tissue is cooled to a temperature in a range from about 0° C. to about −15° C.

15. The method of claim 1, wherein the target tissue is cooled so as to induce apoptosis in the target tissue, and wherein the apoptosis alters a shape of the skin surface.

16. The method of claim 1, further comprising selecting a duration for the remodeling effect, and wherein characteristics of the cooling are determined in response to the selected duration.

17. The method of claim 1, further comprising inserting a plurality of tissue-penetrating probes through the skin surface with a separation between the probes such that the cooling effects the remodeling of the target tissue disposed between the probes.

18. The method of claim 1, wherein the probe comprises an element of a subdermal cryogenic remodeling probe system, the probe system further comprising a cooling fluid supply cartridge coupled with the probe by a cooling fluid path per a controller, and further comprising limiting use of the probe system to treatment of a single patient and disposing of the probe system after treatment of the patient.

19. The method of claim 1, wherein the probe comprises a distal tissue-piercing end, and wherein the piercing comprises inserting the tissue-piercing end into the skin.

20. The method of claim 1, wherein the region of the face comprises the forehead, areas adjacent the eyes, or areas adjacent the mouth.

21. A method for improving a cosmetic appearance of a patient, the patient having a skin surface comprising a region of the face with a muscle therebelow, the muscle having an associated nerve/muscle contractile chain comprising the muscle, a nerve, a connective tissue, and a nerve/muscle junction, the method comprising piercing a probe through the skin surface and directing cooling from the probe to a component of the nerve/muscle contractile chain such that the component is remodeled and the remodeling temporarily inhibits contraction of the muscle so as to mitigate lines and wrinkles in the face associated with contraction of the muscle sufficiently to improve the cosmetic appearance of the face.

22. The method of claim 21, wherein the probe comprises a distal tissue-piercing end, and wherein the piercing comprises inserting the tissue-piercing end into the skin.

23. The method of claim 21, wherein the region of the face comprises the forehead, areas adjacent the eyes, or areas adjacent the mouth.

24. A method for treating a patient, the patient having a skin surface comprising a region of the face and a muscle therebelow, the method comprising piercing a probe through the skin surface and directing sufficient tissue remodeling energy or cooling below the skin surface from the probe so that contraction of the muscle is temporarily inhibited or a loss of elasticity is temporarily induced thereby reducing the appearance of lines and wrinkles in the face associated with contraction of the muscle.

25. The method of claim 24, wherein the tissue remodeling energy or cooling is applied using a cosmetic treatment system, and further comprising disposing of the treatment system after treatment of a single patient.

26. The method of claim 24, wherein the probe comprises a distal tissue-piercing end, and wherein the piercing comprises inserting the tissue-piercing end into the skin.

27. The method of claim 24, wherein the region of the face comprises the forehead, areas adjacent the eyes, or areas adjacent the mouth.

* * * * *